(12) United States Patent
Jessop et al.

(10) Patent No.: US 10,765,493 B2
(45) Date of Patent: Sep. 8, 2020

(54) CHEEK AND LIP EXPANSION DEVICE AND METHOD

(71) Applicant: ULTRADENT PRODUCTS, INC., South Jordan, UT (US)

(72) Inventors: Neil T. Jessop, Sandy, UT (US); Bruce S. McLean, Sandy, UT (US); Craig Hines, Lihue, HI (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 16/030,591

(22) Filed: Jul. 9, 2018

(65) Prior Publication Data

US 2018/0318041 A1    Nov. 8, 2018

Related U.S. Application Data

(63) Continuation of application No. 14/858,954, filed on Sep. 18, 2015, now Pat. No. 10,016,258, which is a continuation-in-part of application No. 14/776,867, filed as application No. PCT/US2017/028083 on Mar. 14, 2014, now Pat. No. 9,901,332.

(60) Provisional application No. 61/789,929, filed on Mar. 15, 2013.

(51) Int. Cl.
    *A61C 5/00*     (2017.01)
    *A61C 5/90*     (2017.01)
    *A61B 1/24*     (2006.01)

(52) U.S. Cl.
    CPC . *A61C 5/90* (2017.02); *A61B 1/24* (2013.01)

(58) Field of Classification Search
    CPC ..... A61C 17/043; A61C 19/06; A61C 19/066; A61B 13/00; A61B 17/0293
    See application file for complete search history.

(56) References Cited

U.S. PATENT DOCUMENTS

| | | | | |
|---|---|---|---|---|
| 5,037,298 A | * | 8/1991 | Hickham | A61C 17/08 433/93 |
| 5,199,872 A | * | 4/1993 | Leal | A61B 1/24 433/136 |
| D496,995 S | * | 10/2004 | Dorfman | A61C 5/90 D24/135 |

(Continued)

OTHER PUBLICATIONS

Communication under Rule 71(3) dated Mar. 5, 2020 in European Patent Application No. 14763277.2.

*Primary Examiner* — Nicholas D Lucchesi
(74) *Attorney, Agent, or Firm* — Maschoff Brennan

(57) ABSTRACT

Cheek and lip expansion devices including an upper frame portion configured to extend about an upper dental arch, and a lower frame portion configured to extend about a lower dental arch. The upper and lower frame portions may each include first and second side members, each with anterior and posterior regions. An upper connecting member may extend between the anterior regions of the upper side members. A lower connecting member may extend between the anterior regions of the lower side members. The posterior regions of the upper and lower side members on respective sides of the frame are joined to one another to form a bendable radius that resists bending at a distinct point. The bendable radius on opposed sides permits the frame to be collapsed top to bottom. The frame may be collapsible side-to-side. A posterior crossbar may be provided extending between the posterior regions of the side members.

20 Claims, 22 Drawing Sheets

(56) References Cited

U.S. PATENT DOCUMENTS

| | | | |
|---|---|---|---|
| 7,300,401 B2 * | 11/2007 | Patrickus | A61C 17/08 600/238 |
| D737,964 S * | 9/2015 | Jessop | D24/135 |
| 9,387,054 B2 * | 7/2016 | Hines | A61B 1/32 |
| 9,901,332 B2 | 2/2018 | Jessop et al. | |
| 10,016,258 B2 | 7/2018 | Jessop et al. | |
| 2002/0022211 A1 * | 2/2002 | Horiguchi | A61C 5/90 433/140 |
| 2004/0209225 A1 * | 10/2004 | Kilcher | A61C 5/90 433/140 |
| 2005/0227199 A1 * | 10/2005 | Patrickus | A61C 17/08 433/93 |
| 2006/0069316 A1 * | 3/2006 | Dorfman | A61C 1/088 600/237 |
| 2006/0155171 A1 * | 7/2006 | Yang | A61B 1/0676 600/238 |
| 2006/0234187 A1 * | 10/2006 | Kilcher | A61C 5/90 433/140 |
| 2007/0148619 A1 * | 6/2007 | Anderson | A61C 17/08 433/136 |
| 2011/0060194 A1 * | 3/2011 | Risto | A61B 1/32 600/210 |
| 2018/0193012 A1 | 7/2018 | Jessop et al. | |

\* cited by examiner

CHEEK AND LIP EXPANSION DEVICE AND
METHOD

CROSS-REFERENCE TO RELATED
APPLICATION

The present application is a continuation of U.S. patent application Ser. No. 14/858,954, filed Sep. 18, 2015 entitled CHEEK AND LIP EXPANSION DEVICE AND METHOD, which is a continuation-in-part of U.S. patent application Ser. No. 14/776,867, filed Sep. 15, 2015, entitled CHEEK RETRACTOR DEVICE AND METHOD", which is a 35 U.S.C § 371 national stage application of PCT Application PCT/US14/28083, filed Mar. 14, 2014, entitled CHEEK RETRACTOR DEVICE AND METHOD" which claims the benefit of U.S. Provisional Patent Application Ser. No. 61/789,929, filed Mar. 15, 2013, entitled "CHEEK RETRACTOR DEVICE AND METHOD". The disclosure of each of the foregoing is incorporated by reference in its entirety.

BACKGROUND

1. The Field of the Invention

The present invention is in the field of dentistry, particularly devices for isolating a patient's teeth from soft oral tissue and enlarging the working field for the practitioner.

2. The Relevant Technology

In certain procedures, particularly certain dental procedures, it can be helpful to retract soft oral tissue of the oral cavity from a patient's teeth so as to create an enlarged working field around the teeth and dental arches. Various retraction devices exist, although these devices share certain problems. They are often difficult to insert and remove, often requiring extensive time to insert and causing discomfort to the patient during insertion and removal. They generally require that a dentist, dental assistant, or other practitioner use both hands to insert and remove the devices. They are generally uncomfortable to patients and can activate patient's pharyngeal reflexes (i.e., gag reflex).

In some cases they simply stretch the lips apart without directly bearing against the cheeks. In such cases, they do not permit further manipulation of the patient's lips or cheeks without causing pain. In other cases, they include bulky lip retraction structures that can block access to tooth surfaces along the sides of a dental arch. In still other cases, they are formed from rigid wires bent into a clam-shell structure that have little flexibility and which can exert significant pressure onto sensitive oral tissue, such as the sulcus between the gingiva and lips.

As such, it would be beneficial to provide a cheek and lip retraction or expansion device exhibiting improved characteristics.

BRIEF SUMMARY

Disclosed herein are cheek and lip retraction or expansion devices for use in dental procedures or other procedures requiring access to the oral cavity with minimal obstruction. Various features are disclosed which may provide collapsibility, ability to latch in a collapsed configuration, and easier insertion into a patient's mouth, (e.g., even allowing insertion with one hand). The device may include structural and/or curvature characteristics which help "pull" the device into a patient's mouth, facilitating easier insertion and maintenance within the mouth once installed.

In an aspect, the cheek and lip retraction or expansion device includes a frame that is flexible and resilient so as to be selectively collapsible and expandable to facilitate insertion into the mouth when in collapsed configuration and retraction or displacement of a person's cheeks and lips from teeth of the upper and lower dental arches when in an expanded configuration. The expanded frame can comfortably bear against and inflate, displace, and/or flare outward the cheeks and lips to provide an opening effect (e.g., an umbrella- or tent-like effect). As used herein, the device may be interchangeably described as a retraction or expansion device. It will be appreciated that the device may tend to expand the cheeks and lips outward and forward (away from the dental arch and other surfaces they normally rest against), without uncomfortably retracting (really stretching) the lips side-to-side, which is what is accomplished by many existing devices.

The frame includes an upper frame portion configured to extend about a person's upper dental arch, so as to bear against and retract soft oral tissue (e.g., cheeks and upper lip) from one or more teeth of the upper dental arch when the frame is in an expanded configuration. The frame also includes a lower frame portion configured to extend about a person's lower dental arch, so as to bear against and retract soft oral tissue (e.g., cheeks and upper lip) from one or more teeth of the lower dental arch when the frame is in an expanded configuration. The upper frame portion includes first and second upper side members, each upper side member including a posterior region and an anterior region. An upper anterior connecting member is positioned between the anterior regions of the first and second upper side members. The lower frame portion similarly includes first and second lower side members, each lower side member including a posterior region and an anterior region. A lower anterior connecting member is positioned between the anterior regions of the first and second lower side members.

The upper side members of the upper frame portion are joined to corresponding lower side members of the lower frame portion at their posterior regions. For example, the first upper and lower side members can be joined on a left side of the frame, and the second upper and lower side members can be joined on a right side of the frame. In some embodiments, the upper and lower side members form a bendable radius in a posterior region of the frame that resists bending at a distinct point so as to create a larger bending radius where the bending moment is spread over a greater length along the upper and lower side members. The first upper and lower side members joined at their posterior regions form a first posterior arced region or joint (e.g., on the left side of the frame). The second upper and lower side members are similarly joined at their posterior regions to form a second posterior arced region or joint (e.g., on the right side of the frame). In some embodiments, the posterior regions of the side members can be thickened in the vicinity of the first and second posterior joints so as to resist bending at distinct points, resulting in bendable radii that spread bending forces out anteriorly towards the anterior ends of the respective side members. In another embodiment, mechanisms other than thickening could be employed to also resist bending (e.g., use of a different material, etc.) Such a configuration permits the upper and lower frame portions to be at least partially collapsed or folded top to bottom, toward each other.

The frame also has a posterior width (e.g., between the first and second posterior joints) that is greater than either or both of the upper and lower anterior width dimensions. Such a configuration of greater posterior width than anterior widths helps to pull the device into the mouth, rather than push it out. By comparison, other cheek or lip retractors exhibit an oppositely configured wedge relationship where the anterior dimensions of the device are greater than the posterior dimensions. Such configurations exhibit a tendency to be easily pushed out of the oral cavity, rather than maintained in the desired position. In addition, they tend to stretch the lips to their greatest possible side-to-side extent, which is both uncomfortable for the patient and unhelpful to the practitioner, as it does not permit the practitioner any additional flexibility to pull one side of the lip (or both sides) to further expand the view and/or working field.

In some embodiments, the frame may further comprise a posterior crossbar positioned between (e.g., interconnecting) first and second posterior regions of the upper and lower frame portions. In some embodiments, the posterior crossbar interconnects the first and second posterior joints between the first and second upper and lower side members, respectively. The posterior crossbar is advantageously flexible and resilient to permit selective side-to-side collapse and expansion of the frame. In this way, the posterior crossbar can assist in providing an expansion force (e.g., in the x-axis direction) to the posterior arced regions of the upper and lower frame portions in order to retract cheeks from a patient's dental arches, particularly in the posterior region of the patient's mouth. The posterior crossbar may include first and second members having a posterior curvature, being joined at essentially a middle portion of the crossbar to create one or more preferential bending regions. The posterior crossbar can be configured and positioned so as to lie behind a person's posterior-most teeth (e.g., second molars in the case of an adult). In this configuration, the posterior crossbar does not extend and form a bridge across a patient's posterior teeth, which can otherwise obstruct and interfere with the ability of the patient to bite down and join occlusal surfaces of upper and lower posterior teeth. The posterior crossbar can also assist in retracting or expanding the patients lips forward (e.g., anteriorly in the z-axis direction) and outwardly from anterior teeth (e.g., incisors and cuspids). It does this by interacting with (e.g., at least partially abutting posterior soft oral tissue associated with the mandibular ramus) to create posterior loading of the flexible spring-like frame to assist in flaring the cheeks and lips outwardly and away from adjacent posterior and anterior teeth of the upper and lower dental arches.

In some embodiments, where a posterior crossbar is provided, a selectively removable tongue guard may be provided that is selectively coupleable to the crossbar, to allow selective attachment or removal of the tongue guard, even with the device expanded, in the mouth.

In some embodiments, the upper frame portion can have an anterior width that is greater than an anterior width of the lower frame portion. For example, the upper anterior connecting member between the first and second upper side members can have a length that is greater than the length of the lower anterior connecting member between the first and second lower side members. This can help accommodate differences between the size and anatomy of the upper and lower dental arches, and the associated vestibules between the dental arch and the cheek and/or lips into which the upper and lower frame portions are placed when the frame is expanded. For example, such a difference in upper and lower anterior widths better accommodates the anatomy into which the frame is placed, where the upper dental arch (and the associated upper anterior vestibule) is typically wider than the lower dental arch (and associated lower anterior vestibule).

In some embodiments, the cheek and lip retraction or expansion device may include an upper lip protecting member disposed on or forming part of the upper anterior connecting member of the upper frame portion and that is configured to extend away from an oral cavity and over an upper lip. A lower lip protecting member may similarly be disposed on or form part of the lower anterior connecting member of the lower frame portion in a manner to extend away from the oral cavity and over a lower lip. In some embodiments, the lip protecting members may be selectively engagable with one another (e.g., corresponding latching structure may be provided on each) when the upper frame portion is folded towards the lower frame portion so as to temporarily latch the upper and lower frame portions together. This can aid the practitioner and facilitate insertion of the retraction or expansion device using one hand. For example, latching the upper and lower members can free up a hand that might otherwise be required to collapse the upper and lower members together (e.g., in the y-axis direction) while using one hand to collapse the frame from side-to-side (e.g., in the x-axis direction).

These and other benefits, advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 15A shows one side of the device of FIG. 12A being placed (e.g., shoe-horned) into a person's mouth.

FIG. 15B is a progression from the state shown in FIG. 15A, showing the other side of the frame being positioned into the person's mouth.

In FIG. 16A, the upper and lower frame portions have been collapsed and latched together, and the posterior arced regions pressed together, collapsing the device side-to-side, as well as top to bottom.

DETAILED DESCRIPTION

I. Introduction

The invention generally relates to intra-oral cheek and lip expansion devices useful for expansion of soft oral tissues away from the dental arches, isolating one or more teeth from soft oral tissue and creating an enlarged working field. Such cheek and lip expansion devices may include a selectively collapsible and expandable flexible and resilient (e.g., spring-like) frame for insertion into an oral cavity. The collapsed configuration facilitates insertion into the mouth, while the expanded configuration, while positioned in the mouth, allows the frame to bear against and retract or displace soft oral tissue in multiple dimensions and thereby isolate one or more teeth from soft oral tissue and create an enlarged working field. For example, rather than moving the mandible down, the cheeks and lips may be displaced outward and forward in order to enlarge the working field, increasing space for the practitioner to work and/or visualize the teeth, gums, or other structure.

The frame may include an upper frame portion and a lower frame portion, which are advantageously flexible and resilient (e.g., spring-like) so as to selectively assume collapsed and expanded configurations during installation and use, as discussed more fully below. The flexibility of the upper and lower frame portions permits them to be selectively collapsed in a side-to-side (e.g., x-axis) direction and also an up-and-down (e.g., y-axis) direction to facilitate insertion of the frame, when in a collapsed configuration, into the oral cavity of a patient. After installation, the resiliency of the upper and lower frame portions causes them to expand outwardly in a spring-like fashion in at least x-axis and y-axis directions to assume an expanded configuration inside the patient's oral cavity. The expanded frame inflates the patient's mouth (e.g., like a tent or umbrella), displacing, comfortably flaring, and retracting the cheeks and lips away from teeth of the upper and lower dental arches. Posterior loading, such as by abutment of a posterior regions of the frame against a posterior region of the patient's mouth, may cause the frame to also exert force in a forward (or z-axis) direction in order to retract the patient's lips away from teeth in the forward direction. In this way, the expansion device can create an enlarged and unobstructed working field in the oral cavity by retracting the cheeks and lips from a patient's teeth in a comfortable, umbrella-like fashion, instead of unnecessarily, excessively, and uncomfortably stretching the lips too far in a side-to-side (x-axis) direction, as typically occurs with prior lip retraction devices.

II. Exemplary Cheek and Lip Expansion Devices

Figure 1:
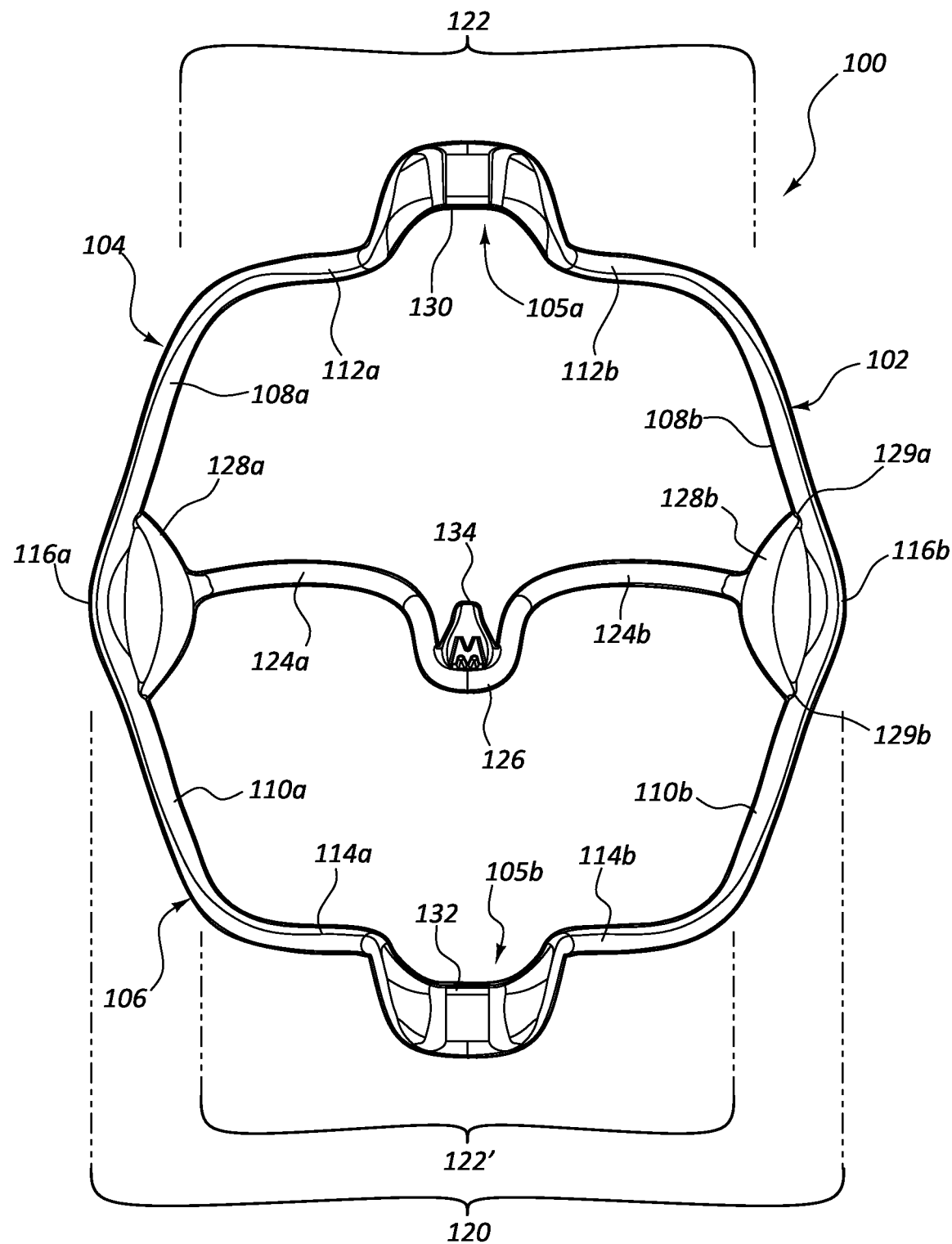
FIG. 1 is an anterior view of an exemplary expanded cheek and lip expansion device.

FIGS. 1 through 5 illustrate an exemplary cheek and lip expansion device 100. FIG. 1, for example, shows a cheek and lip expansion device 100 comprising a frame 102 for insertion into an oral cavity (oral cavity and mouth may generally be interchangeably used herein). Frame 102 further includes an upper frame portion 104 and a lower frame portion 106, which are advantageously flexible and resilient so as to selectively assume collapsed and expanded configurations during installation and use. In a collapsed configuration (e.g., see FIG. 3 and FIGS. 13A-14B), device 100 is more easily inserted into the oral cavity, while the expanded configuration (e.g., see FIG. 5) allows upper and lower frame portions 104, 106 to extend about the upper and lower dental arches, respectively, and to bear against and retract soft oral tissue from adjacent teeth in multiple dimensions (e.g., in each of x-axis, y-axis, and z-axis directions) to create an enlarged working field for the practitioner. Absent applied forces (or engagement of an optional latching mechanism discussed below), frame 102 may assume the expanded configuration seen in FIGS. 1-4. The expanded frame 102 inflates or dilates the patient's mouth, displacing, flaring, and retracting tissue including the cheeks and lips away from the jaw and the teeth of the upper and lower dental arches. Posterior loading, such as by abutment of a posterior end of frame 102 against a posterior region of the patient's mouth, causes frame 102 to also exert force in a forward (or z-axis) direction in order to retract the patient's lips away from teeth in the forward direction.

As further illustrated in FIG. 1, upper frame portion 104 includes upper side members 108, including a first (e.g., left) upper side member 108a and a second (e.g., right) upper side member 108b. Similarly, lower frame portion 106 includes lower side members 110, including a first (e.g., left) lower side member 110a and a second (e.g., right) lower side member 110b. References to "left" and "right" are made from the perspective of the practitioner facing the patient, although it is to be understood that the designation is arbitrary; the frame of reference could alternatively be made from the perspective of the patient line of sight (i.e., right becomes left and vice versa).

The upper side members 108 and lower side members 110 extend from arced regions 116a and 116b. The first upper and lower side members 108a, 110a may be joined at a first posterior frame region 116a, and the second upper and lower side members 108b, 110b may be joined at a second posterior frame arced region 116b. Posterior frame arced regions 116 may form flexible yet sufficiently rigid joints that resist bending at a single point but rather distribute the bending radius along a substantial length of upper and lower side members 108, 110 when upper and lower frame portions 104, 106 are collapsed together. This in turn distributes opening forces along a substantial portion of the length of each side member in order to bear against and effectively retract soft oral tissues from the patient's teeth in both posterior and anterior regions of the mouth. In another embodiment, a posterior hinge may be provided that enables articulation between the upper and lower side members 108 and 110.

In some embodiments, posterior frame arced regions 116 may each form a curved, bowed, v-shaped or u-shaped posterior joint on either side of frame 102. While posterior frame arced regions 116 may be generally described as forming "v-shaped" or "u-shaped" posterior joints, these terms are to be construed broadly. For example, any acute angular relationship between upper and lower side members 108, 110 may be considered to be v-shaped or u-shaped. In addition, even if the angular relationship between upper and lower side members 108, 110 were technically obtuse rather than acute, the terms "v-shaped" and "u-shaped" may be used to broadly encompass any such configurations so long as the radius of curvature between upper and lower side members 108, 110 is smaller at the posterior end or region of frame 102 compared to the anterior end or region. In some embodiments, posterior frame arced regions 116 may represent the posterior most portions of upper and lower frame portions 104, 106.

The upper frame portion 104 may include an upper anterior connecting member 112, which may be disposed between anterior regions of first and second upper side members 108a, 108b and which may include a first upper connecting portion 112a adjacent to first upper side member 108a and a second upper connecting portion 112b adjacent to second upper side member 108b. Similarly, the lower frame portion 106 may include a lower anterior connecting member 114, which may be disposed between anterior regions of the first and second lower side members 110a, 110b and which may include a first lower connecting portion 114a and a second lower connecting portion 114b.

The distance between a central point, apex or posterior-most region of the first and second posterior frame arced regions 116a, 116b defines a posterior width 120 of frame 120. The distance between anterior-most regions of first and second upper side members 108a, 108b of upper frame portion 104 defines an upper anterior width 122. The distance between the anterior-most region of first and second lower side members 110a, 110b of lower frame portion 106 defines a lower anterior width 122'. In some embodiments, the posterior width 120 of frame 102 as defined between upper and lower side members 108, 110 adjacent posterior frame ends 116 (e.g., the distance between the vertex of angled first posterior frame end or joint 116a to the vertex of angled second posterior frame end or joint 116b) is greater than the upper and lower anterior widths 122, 122' of upper and lower frame portions 104, 106.

In some embodiments, the upper and lower anterior widths 122, 122' of upper and lower frame portions 104, 106, respectively, can also differ from one another. In some embodiments, the upper anterior width 122 of upper frame portion 104 can be greater than the lower anterior width 122' of lower frame portion 106, such as to account for anatomical differences in size between a patient's upper and lower dental arches, with the upper dental arch typically being wider and encompassing or surrounding the lower dental arch in the anterior region when the teeth are brought together, with the upper incisors and cuspids generally extending over and forward of the lower incisors and cuspids.

Expansion device 100 may be designed to have different sizes depending on the facial anatomy of the patient (which may be determined, for example, by the spacing between the eyes and/or whether the patient is a small child, growing child, or adult). In some embodiments, expansion device 100 may have a posterior width 120 in a range of about 90-130 mm (e.g., about 95-110 mm, about 100 mm, or about 115-120 mm) and anterior widths 122, 122' in a range of about 50-90 mm. For example, the upper anterior width 122 of upper anterior connecting member 112 may be in a range of about 70-90 mm. Where the lower anterior width 122' of lower anterior connecting member 114 is less than the upper anterior width 122 of upper anterior connecting member 112, it may be in a range of about 50-90 mm. In some embodiments, the posterior width 120 may be from about 20% to about 100%, from about 20% to about 80%, from about 25% to about 75%, or from about 30% to about 50% (e.g., about 40%-50%) greater than either the upper or lower anterior widths 122, 122'. In some embodiments, the posterior width 120 can be greater than the upper anterior width 122, which may be greater than the lower anterior width 122'. By way of example, with a posterior width of about 100 mm, an upper anterior width of about 70 mm, and a lower anterior width of about 50-55 mm, the posterior width 120 is about 40% greater than the upper anterior width 122, and about 90-100% greater than the lower anterior width 122'. The upper anterior width 122 may in turn be from about 15% to about 80%, from about 25% to about 75%, or from about 30% to about 50% (e.g., about 40%) greater than the lower anterior width 122'. Providing a greater upper anterior width 122 as compared to lower anterior width 122' better conforms to the actual anatomy of a typical patient, as the upper dental arch is typically wider across its anterior region than the lower dental arch. This configuration provides better comfort and a better fit as upper and lower connecting members 112, 114 are received within corresponding upper and lower anterior vestibules of the mouth.

In addition, a larger posterior width 120 advantageously provides a configuration by which expansion device 100 tends to pull itself into the patient's mouth and be retained therein, as opposed to exhibiting a tendency for a cheek or lip retractor to be pushed out of the patient's mouth, which is typical of many existing devices. In addition, this feature helps improve the ease of insertion of expansion device 100, particularly in combination with the side-to-side collapsibility that may be provided by the flexible and resilient spring-like frame 102. For example, the posterior width 120 can be collapsed side-to-side to have a width that is less than anterior widths 122, 122' during insertion, if desired (see FIGS. 14B and 16A), and then the posterior width 120 expands once released within the mouth, helping to pull the device back into the mouth, and to maintain it there so long as desired.

Figure 6:
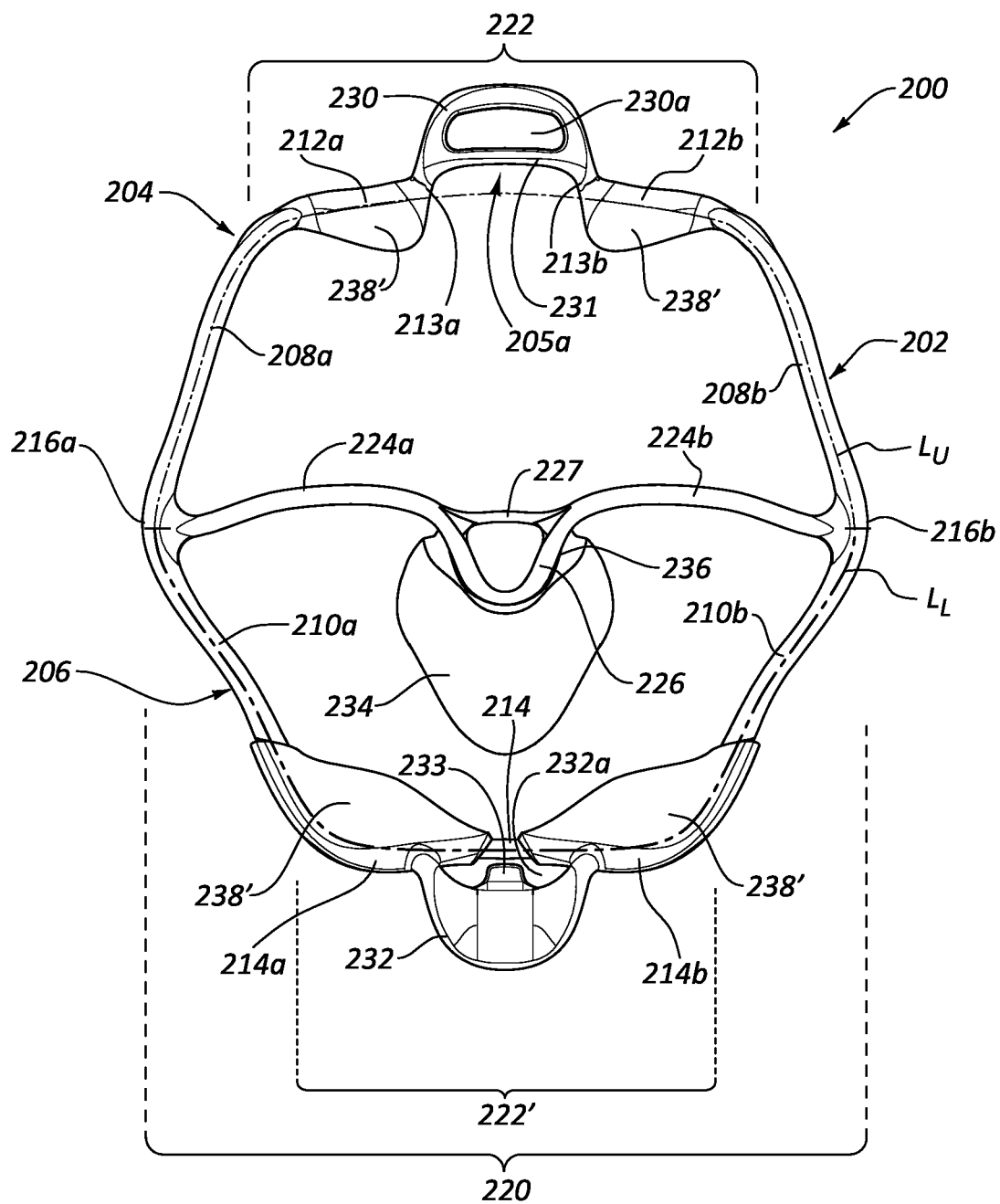
FIG. 6 is an anterior or front view of an alternative exemplary expanded cheek and lip expansion device.
Figure 7:
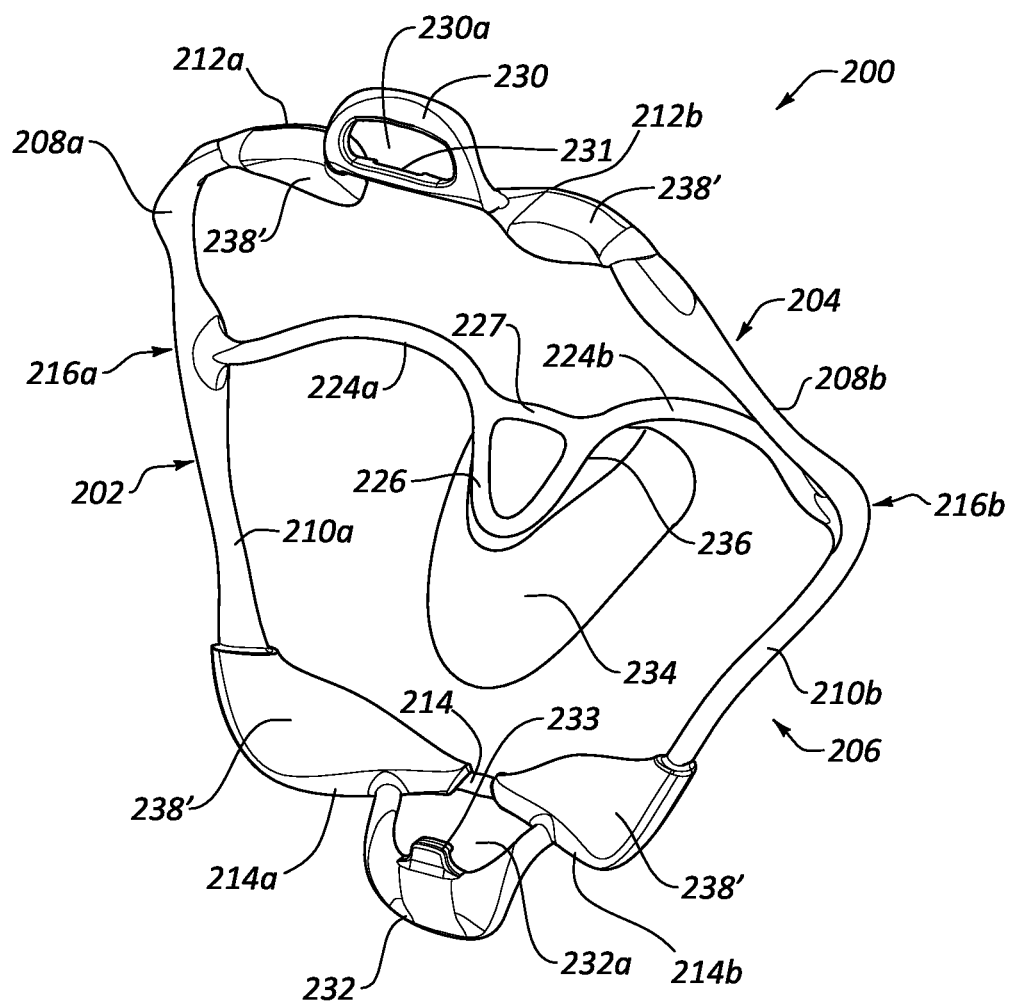
FIG. 7 is a front perspective view of the cheek and lip expansion device of FIG. 6.

In addition to or instead of the upper anterior width 122 being greater than the lower anterior width 122', the total length of upper frame portion 104 can be greater than the total length of lower frame portion 106. In some embodiments, the total length of upper frame portion 104 is the combined lengths of first and second upper side members 108 and upper anterior connecting member 112, and the total length of lower frame portion 106 is the combined lengths of first and second lower side members 110 and lower anterior connecting member 114. The overall lengths of upper and lower frame portions are shown in FIG. 6, which shows another embodiment of a cheek and lip expansion device. The overall length of the upper frame portion is designated $L_U$, while the overall length of the lower frame portion is designated $L_L$. Differences in length between upper and lower frame portions 104, 106 can account for anatomical differences in length and size between the upper and lower dental arches of a patient, and the associated upper and lower vestibules of a typical patient. Many existing cheek or lip retraction devices do not account for such differences, but rather mirror the bottom half of the device relative to the top half, which decreases both effectiveness and comfort.

To further account for anatomical differences between upper and lower dental arches, side members 108, 110 of upper and lower frame portions 104, 106 may differ from one another in length. For example, side members 108 of upper frame portion 104 may be somewhat shorter or longer than side members 110 of lower frame portion 106. For example, upper side members 108 may be shorter than lower side members 110, although upper frame portion 104 may have an anterior width 122 and overall length that are greater than the anterior width 122' and overall length of lower frame portion 106, as described above. All such characteristics may be provided to better fit the anatomy of the upper and lower dental arches and associated upper and lower vestibules into which the upper and lower frame portions are received. They can be customized based on differences in anatomy, size, age, gender, and the like.

As illustrated in FIG. 1, frame 102 may include a posterior crossbar 124 positioned between first and second posterior ends 116a, 116b. In some embodiments, the crossbar 124 may include first and second posteriorly curved portions 124a, 124b. Posterior crossbar 124 may include a curved, bowed, v-shaped or u-shaped anteriorly curved portion 126 (e.g., centrally located along posterior crossbar 124 between the first and second curved portions 124a, 124b, if present). Each of the posteriorly curved portions 124a, 124b and the anteriorly curved portion 126 may increase flexibility and resilience of the posterior crossbar 124 to better facilitate side-to-side collapse of frame 102 (e.g., by moving first and second posterior ends 116a, 116b toward each other). Thus, frame 102 may be collapsible in a side-to-side dimension (e.g., x-axis direction) as well as a top-to-bottom dimension (e.g., y-axis direction). Such multi-dimensional collapsibility greatly improves the ease of insertion, facilitating single-handed insertion and installation in a patient's mouth. Single-handed insertion can be further facilitated by providing a latch mechanism, which can latch upper and lower frame portions 104, 106 together, as described in further detail below. A latch mechanism could also be provided for holding frame 102 in a side-to-side collapsed configuration if desired. Such collapsed configuration is described in further detail in conjunction with FIGS. 13A-14B.

In an embodiment, posterior crossbar 124 may be connected to either side of upper frame portion 104 and lower frame portion 106 by first and second floating gussets 128a, 128b, which provide a pair of connections bridging first and second posterior ends or joints 116a, 116b. For example, second floating gusset 128a may connect with right upper side member 108b at upper connection point or region 129a and with right lower side member 110b at lower connection point or region 129b. First floating gusset 128a may be similarly connected with upper and lower side members 108a, 110a. Floating gussets 128 may provide additional rigidity that increases upward, opening curvature or force to frame 102, resists collapse, and directs applied collapsing forces away from (or anterior to) posterior ends or joints 116 and toward connection points or regions 129a, 129b on each side of the floating gusset. Such structure may direct bending of upper and lower frame portions 104, 106 as they are selectively collapsed or expanded in a top to bottom dimension (e.g., y-axis direction). Floating gussets 128 may also facilitate easier side-to-side collapsibility when applying side-to-side forces, as posterior crossbar 124 is not directly connected to upper and lower frames 104, 106 at posterior ends 116 but at points spaced apart from the apex or vertex of posterior ends 116.

Upper and lower frame portions 104, 106 may further include upper and lower lip protecting members 130 and 132, respectively. Upper lip protecting member 130 may be centrally disposed on or in upper anterior connection member 112 (e.g., between first upper connecting portion 112a and second upper connecting portion 112b) and extend laterally forward from upper frame portion 104 in order for upper lip protecting member 130 to extend away from the patient's oral cavity and over the patient's upper lip during use. Lower lip protecting member 132 may be similarly disposed along lower anterior connection member 114 or lower frame portion 106 so as to extend away from the patient's oral cavity and over the patient's lower lip during use.

Upper and lower lip protecting members 130, 132 may curve over and protect the central portion of a patient's upper and lower lips during a dental procedure. In addition, as perhaps best seen in FIG. 1, lip protecting members 130 and 132 may provide recesses or troughs 105a and 105b above and below generally horizontal anterior lines defined by anterior connecting members 112, 114 of upper and lower frame portions 104, 106, respectively. Such troughs can be designed to further enlarge the working field available to the practitioner in the region of the patient's upper and/or lower incisors, while at the same time covering and protecting the central portion of the patient's lips. In at least the case of the upper recess or trough 105a, it may also avoid irritating contact with the bony structure in the central portion of the upper vestibule where the recess 105a is disposed when in the mouth. In an embodiment, lip protecting members 130, 132 may be made from a stiffer material than other frame portions of device 100, which are relatively flexible and resilient. In addition to the benefits described above, lip protection members 130 and 132 may also serve as an emergency removal handle should the device need to be removed quickly. Even where quick removal may not be needed, lip protection members may present a portion of structure 100 that may be easily and readily grasped by the practitioner when the device is to be removed. Advantageously, these members may be the only structure protruding from the person's mouth during use, with the lip protection members covering the central portion of the person's upper and lower lips, rather than the sides thereof, so as to not unnecessarily stretch the patient's lips open from side-to-side to the extent that many other retraction devices do.

Figure 3:
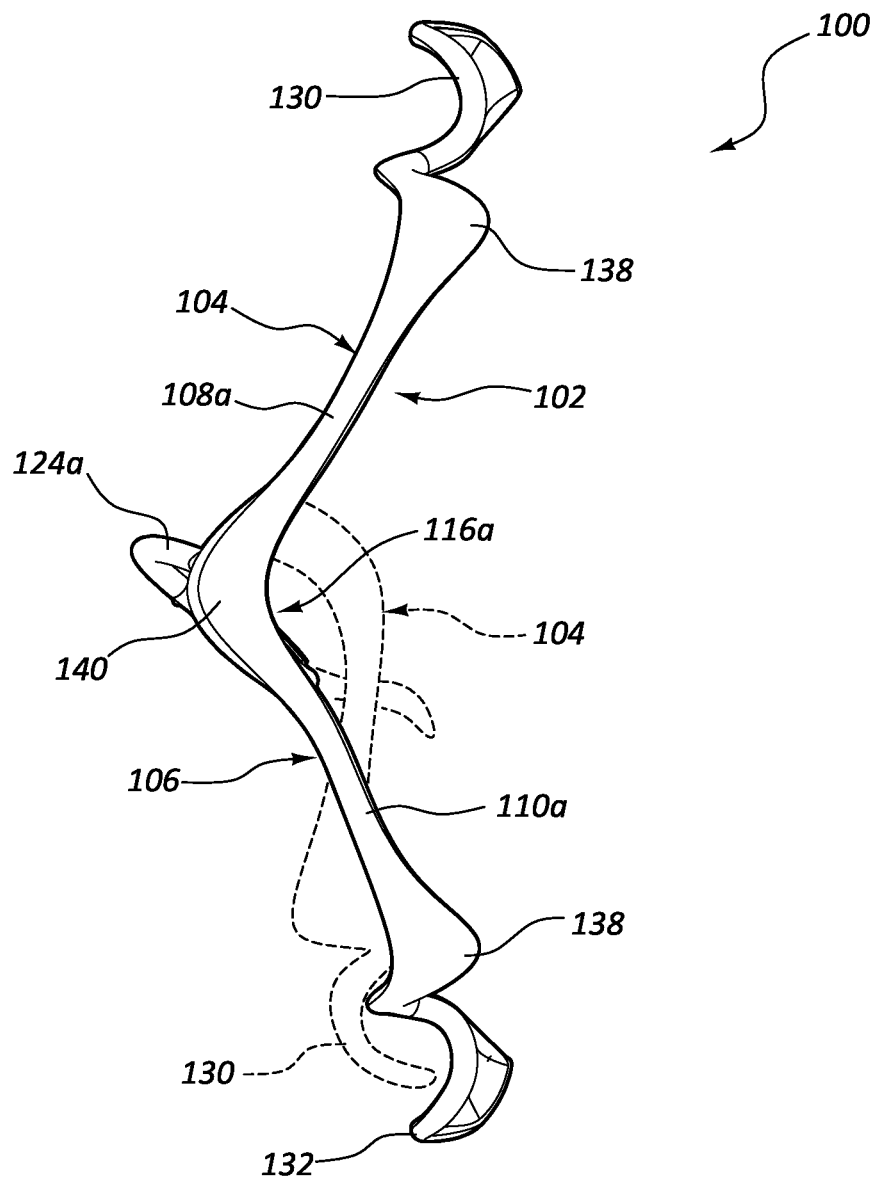
FIG. 3 is a side view of the cheek and lip expansion device of FIG. 1, with the upper frame portion also shown in broken lines indicating how it may be folded and latched with the lower frame portion.
Figure 4:
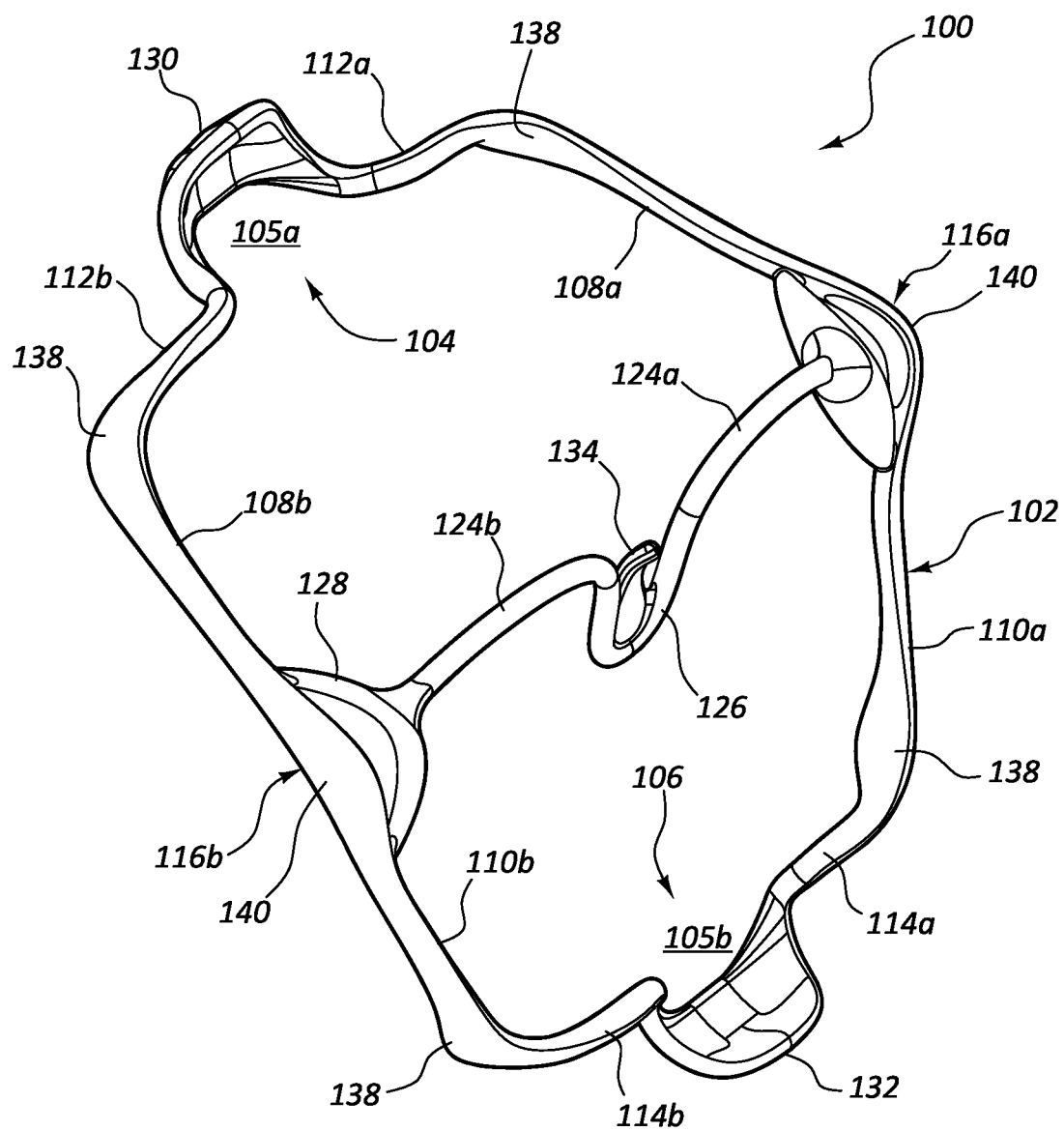
FIG. 4 is a posterior or rear perspective view of the cheek and lip expansion device of FIG. 1.

Furthermore, as perhaps best seen in FIG. 3, lip protecting members 130, 132 may be selectively engagable with one another when upper frame portion 104 is folded towards lower frame portion 106 so as to latch upper 104 and lower 106 frame portions together. Of course, while sometimes described herein in terms of upper frame portion 104 being folded downward towards lower frame portion 106, it will be understood that one or both frame portions may move during such collapse so that lower frame portion 106 may similarly be collapsed toward upper frame portion 104.

Figure 13A:
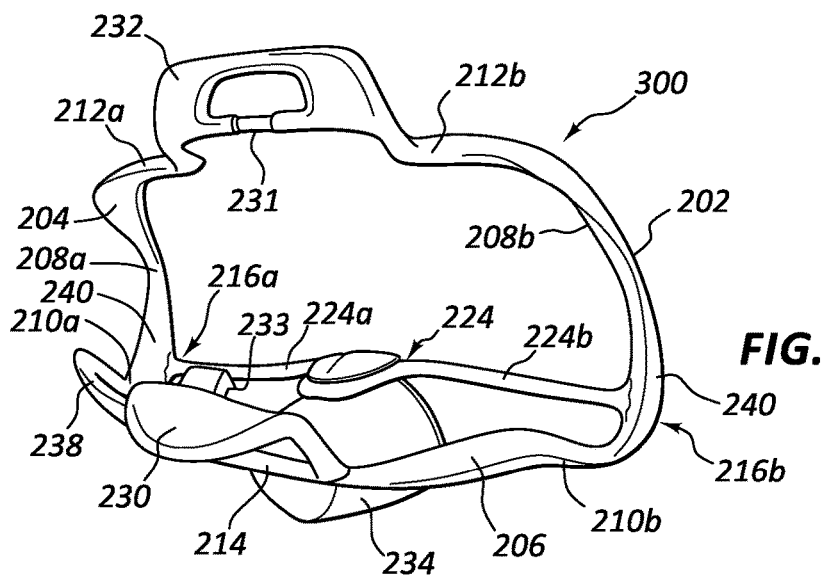
FIG. 13A shows the device of FIG. 12A, with the frame partially collapsed from top to bottom.
Figure 13B:
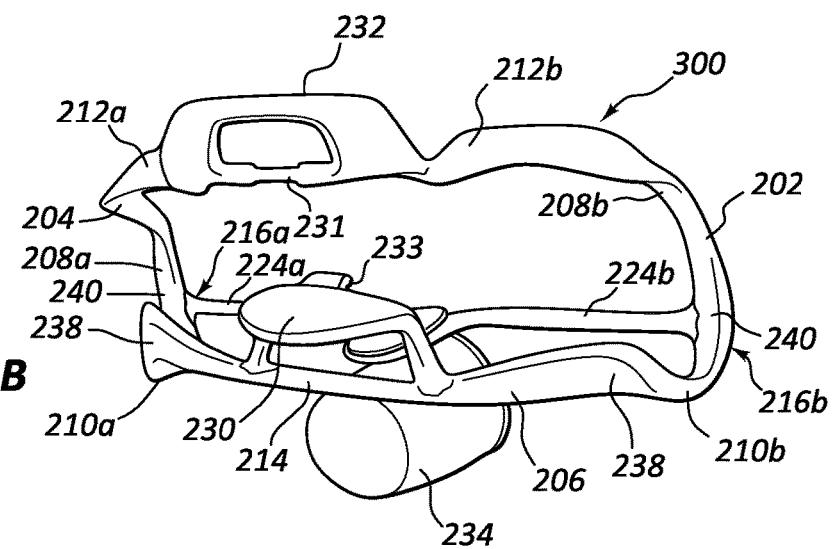
FIG. 13B shows the device of FIG. 13A, showing a greater degree of collapse from top to bottom.
Figure 13C:
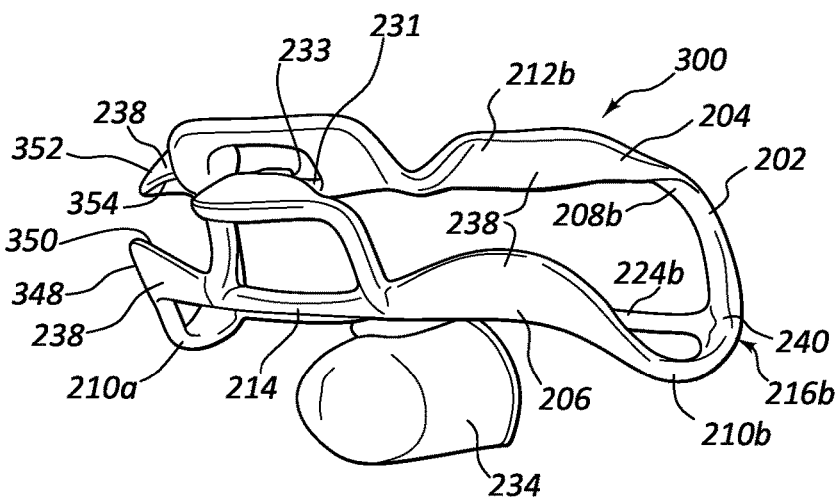
FIG. 13C shows the device of FIG. 13A, showing full collapse of the frame from top to bottom, with the lower frame portion latched to the upper frame portion.

An example of such folding and latching is illustrated in FIG. 3, where the expansion device is shown both before folding (in solid lines), and after folding (with the upper frame portion 104 shown again in broken lines). FIGS. 13A-13C, described in further detail below, further illustrate top to bottom collapse of another similar cheek and lip expansion device. Such a latching mechanism may be used to lock upper and lower frame portions 104, 106 in a closed, collapsed configuration prior to insertion into the patient's mouth. As a result of the device being latched in a configuration where it is collapsed in the upper-to-lower dimension, the practitioner is not required to hold the device in this collapsed configuration (it may be maintained until released), allowing the practitioner to more easily configure and hold the device in a side-to-side collapsed configuration during insertion. Such methods of insertion are described in further detail below in conjunction with FIGS. 15A-16B.

Once cheek and lip expansion device 100 is inserted into the patient's mouth, the latch mechanism may be released to allow frame 102 to expand within the patient's mouth. For example, if upper 104 and lower 106 frame portions are latched together, a practitioner may use one hand to squeeze posterior sides of frame 102 together in a side-to-side manner, and insertion may be easily done with one hand, if such insertion is desired. Of course, two-handed insertion is also possible. Different mechanisms for latching upper and lower frame portions 104, 106 (e.g., a latch structure separate from any lip protection members) may alternatively or additionally be provided. Such additional latch structure could also be provided for latching any side-to-side collapse of any of the devices disclosed herein, as well. Some such latching mechanisms are described in further detail in conjunction with the embodiments of FIGS. 6-16B, below.

Expansion device 100 may also include a tongue guard 134, which may be selectively removable. For example, this may allow attachment or removal of tongue guard 134 from posterior crossbar 124, even while expansion device 100 is installed within an oral cavity of a patient. While tongue guard 134 may be removed while device 100 is installed within an oral cavity of a patient, it may also be removed prior to insertion, after insertion or removal, or at any point in the procedure. Tongue guard 134 may be coupleable to posterior crossbar 124 through any suitable mechanism (e.g., friction fit, press-fit, keyed coupling, etc.). For example, a protrusion and receptacle configuration shared between tongue guard and posterior crossbar 124 may allow tongue guard 134 to "click" into place once seated.

Tongue guard 134 may serve to prevent activation of a patient's pharyngeal reflexes (i.e., gag reflex) and to prevent the flow of saliva. In some patients with a sensitive or "strong" pharyngeal reflex, it may be desirable to remove tongue guard 134 from the expansion device 100. A removable tongue guard 134 permits expansion device 100 to be used with or without tongue guard 134, depending on patient need or preference. In an embodiment, aspiration may be provided through tongue guard 134 (e.g., it may include perforations or holes formed therethrough). Tongue guard 134 may be formed of the same or a different material than other portions of expansion device 100. For example, a material that is particularly flexible, soft and adaptable (e.g., silicone or a thermoplastic elastomer) may be preferred. While tongue guard 134 is shown as a simple stop against which the tongue may press, in other embodiments, the tongue guard may partially or substantially fully encapsulate or envelop at least a portion of the tongue, such as the distal end of the tongue. Examples of such tongue guards (e.g., tongue guard 234) are described in further detail below, in conjunction with FIGS. 6-16B. The tongue guard may advantageously be supported on posterior crossbar 124 in a manner that permits it to move somewhat up, down, or from side-to-side (e.g., to allow the patient some ability to move the tongue during a procedure). A tongue guard and the central portions of crossbar 124 (e.g., anteriorly curved portion 126) may push forward as device 100 is collapsed side-to-side, as apparent in FIGS. 14A-14B. Upon relaxation of such a side-to-side collapsing force, the tongue guard and central portions of cross bar 124 may again move backward (posteriorly) as frame 102 is expanded.

Figure 2:
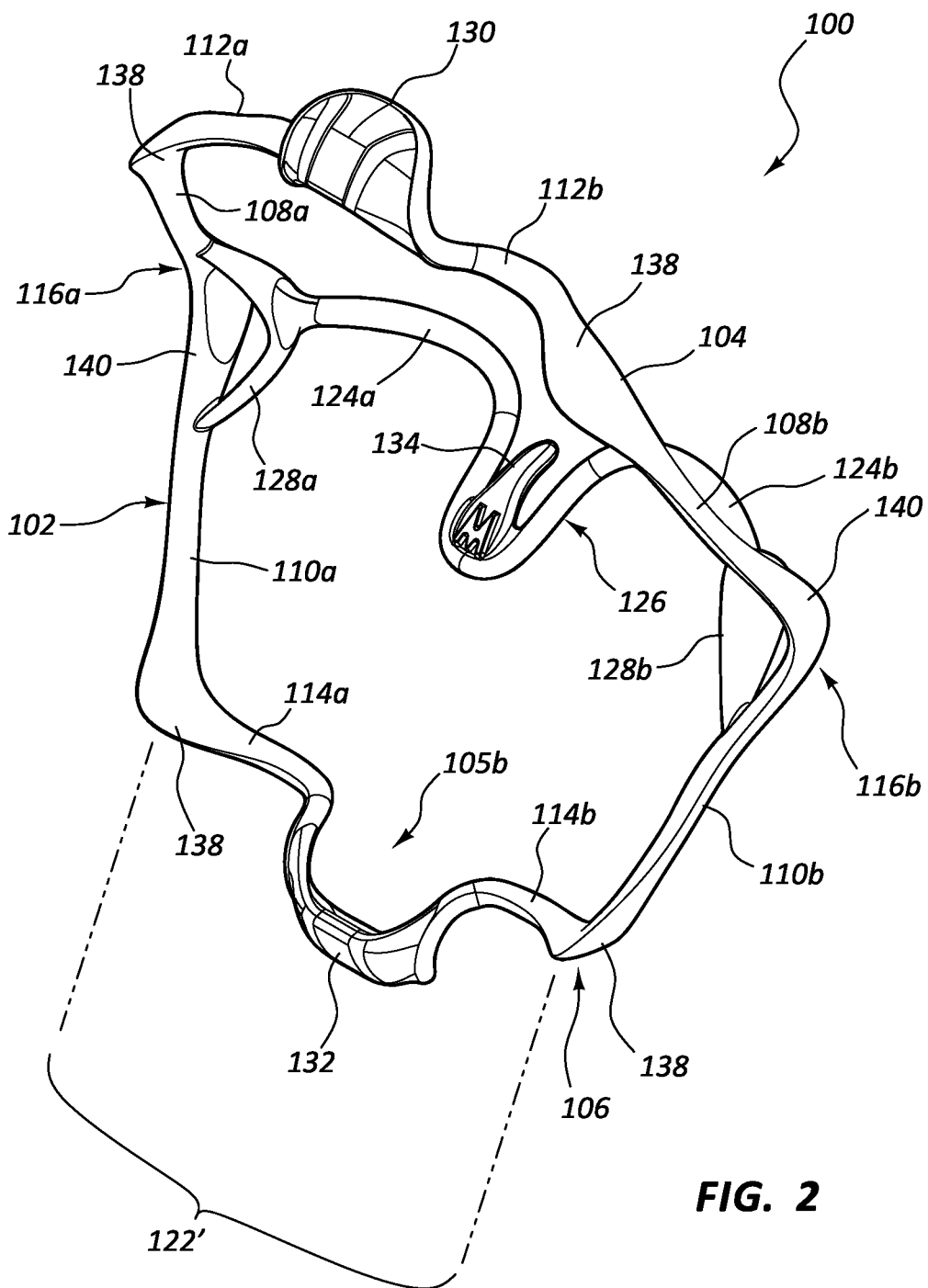
FIG. 2 is a front perspective view of the cheek and lip expansion device of FIG. 1.

As well illustrated in FIGS. 2 and 3, expansion device 100 may also include one or more bumpers or enlarged, thickened portions 138 on frame 102, positioned for receipt into the anterior corners of the upper and lower vestibules (e.g., the area between the teeth and dental arch lips, and cheeks) at anterior corners of the upper and lower frame members. Such bumpers 138 may also provide increased surface area to which a cushioning material may be applied (e.g., a cover over the bumpers), to provide additional cushioning to specific areas of the mouth. The embodiment of FIG. 6 illustrates such bumper covers 238' over the bumpers. For example, a pair of anterior thickened bumpers 138 on each of upper and lower frame portions 104, 106 may be provided at anterior corners where side members 108, 110 intersect with anterior connecting members 112, 114. In addition, left and right side members 108a, 108b may be thickened in various regions, such as adjacent to posterior ends 116 to form thickened posterior regions 140. Bumpers 138 and thickened posterior regions 140 may comprise enlarged, thickened portions of frame 102 as compared to adjacent portions of frame 102, to increase surface area contact with soft tissues in these regions, providing increased comfort as bumpers 138 bear against soft oral tissue. The thickened characteristics of the these thickened regions may also increase their rigidity and resistance to bending as compared to adjacent, thinner regions of the frame. Such increased rigidity aids in lip lifting and retraction or expansion, forcing the lips to flare upwardly and forwardly.

Thickened regions 140 at posterior ends 116 may resist bending at a distinct point of posterior ends or joints 116, so as to form a bendable radius that resists bending at a single distinct point, but rather distributes the bending forces anteriorly, along the length of the side members 108, 110. Some bending forces may also be distributed to regions near or adjacent to upper and lower anterior connecting members 112, 114. Such bending forces may particularly cause bending to occur at more anterior, thinner portions of the side members 108, 110 (e.g., within the thinner central portions of side members 108 and 110) during top to bottom collapse. Bumpers 138 and/or thickened posterior regions 140 at posterior ends 116 may also provide improved access to the oral cavity by the practitioner, better holding back adjacent soft tissue. During use, first and second lower side members 110a, 110b of lower frame portion 106 may reside within the lower facial vestibule, and first and second upper side members 108a, 108b of upper frame portion 104 may reside within the upper facial vestibule. Upper and lower anterior connecting members 112, 114 may reside within the upper and lower anterior vestibules, respectively. Thickened posterior regions 140 may bear against the rear of the facial vestibules, pushing the device forward, with thickened bumpers 138 residing in the corners at the transitions between the facial portion and anterior portion of the upper and lower vestibules. Such bumpers 138 may aid in holding the soft tissues back from the teeth, and flaring the lips and cheeks forward and outwardly.

Anterior bumpers 138 may be located at or near anterior corners of upper and lower frame portions 104, 106 so that upper and lower anterior bumpers 138 serve to cushion the anterior cheek soft tissue adjacent the corners of the patient's mouth. The thickened posterior regions 140 similarly cushion the posterior cheek soft tissue towards the back of the patient's mouth, adjacent the jaw, backwall of the vestibule, and the ramus.

Figure 5:
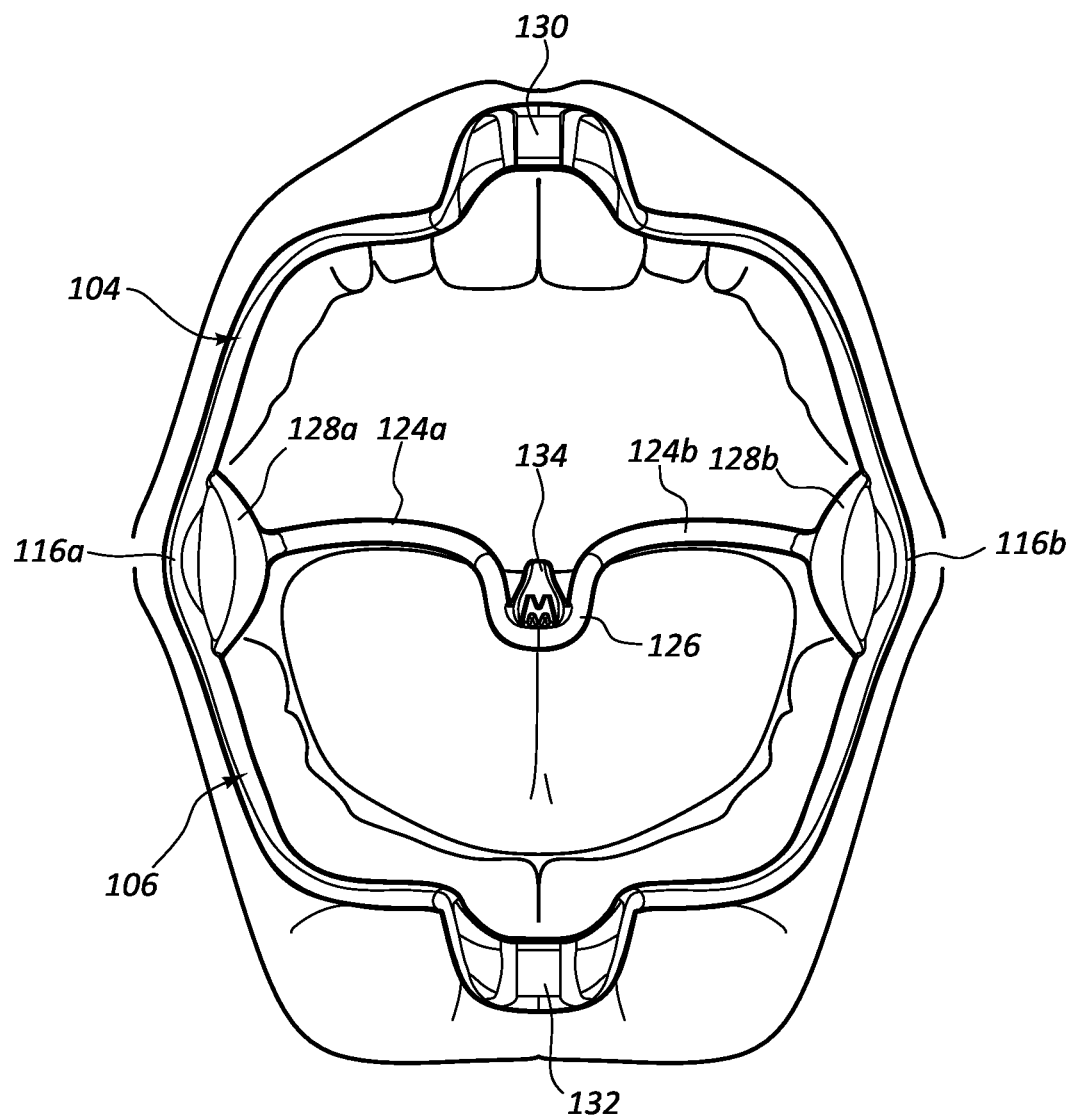
FIG. 5 is an anterior or front view of the cheek and lip expansion device of FIG. 1 installed within the oral cavity of a patient.

Many existing retraction devices tend to "grab" the corners or far sides of the patient's mouth, uncomfortably stretching the lips in a side-to-side dimension. Bumpers 138 aid in reducing or eliminating any such tendency, greatly increasing the comfort of the device as compared to available alternatives. In addition, as seen in FIG. 5, there are no structures at the sides of the opening of the mouth that wrap around or grab the lips, forcing them far open side-to-side, as do many other devices. Rather, the only engagement with the outside of the lip occurs at the top and bottom of the mouth, with lip protecting members 130, 132. In addition, many retractors include a large continuous round or oval ring that extends about the lips on the anterior portion of the mouth to stretch the lips open. Such a ring pulls the lips side-to-side, causing them to be stretched open side-to-side to an uncomfortable degree. The sides of such a ring do not rest within upper or lower vestibules, but pass therebetween. No such anterior ring is necessary or required with the present frame. Rather, the upper and lower frame portions may reside entirely within the upper and lower vestibules.

FIGS. 6 through 11 illustrate another exemplary cheek and lip expansion device 200, similar to device 100. Device 200 similarly includes a flexible and resilient (e.g., spring-like) frame 202 that is selectively collapsible and expandable. Frame 202 may include an upper frame portion 204, which may extend about the upper dental arch and bear against and retract cheeks and/or lips from teeth of the upper dental arch, and a lower frame portion 206, which extends about the lower dental arch and retracts cheeks and/or lips from the jaw and teeth of the lower dental arch. Upper frame portion 204 may include first or left side member 208a and right or second side member 208b. Similarly, lower frame portion 206 may include left or first side member 210a and right or second side member 210b. First side members 208a, 210a may be joined to one another at their posterior ends to form a first posterior frame end or joint 216a, and second side members 208a, 210b may be joined to one another at their posterior ends to form a second posterior frame end or joint 216b on an opposite side of frame 202. While described for simplicity as including various distinct portions or members, it will be appreciated that in some embodiments, any number of such sections or parts of the frame 202, or the entire frame 202, may be a one-piece, monolithic, or unibody structure, e.g., that may be integrally formed from a single piece of material (e.g., injection molded as such). Thus, where various ends or joints are described, it will be appreciated that such members or portions need not actually be separate, and then joined together (although such is certainly also possible)

An upper anterior connecting member 212 may be disposed between the anterior regions of upper side members 208a, 208b. A lower anterior connecting member 214 may be disposed between the anterior regions of lower side members 210a, 210b. Upper anterior connecting member 212 may include first upper connecting portion 212a adjacent to first upper side member 208a and a second upper connecting portion 212b adjacent to second upper side member 208b, while lower anterior connecting member 214 may include first lower connecting portion 212a adjacent to first upper side member 208a and a second lower connecting portion 212b adjacent to second upper side member 208b. Upper anterior connecting member 212 is shown as being upwardly extended adjacent the central portion of upper frame portion 204 (e.g., corresponding to upper lip protecting member 230), rather than simply running generally horizontally across the anterior side (as line $L_U$ does). Such upward extensions 213 create an additional recessed space 205a adjacent the upper anterior connecting member 212 and upper lip protecting member 230. This space advantageously keeps the upper anterior connecting member 212 from uncomfortably contacting bone in this region of the anterior upper vestibule. The lower anterior connecting member 214 is shown as extending generally horizontally across this analogous space, as the upper and lower vestibule anatomy is different. Of course, if desired, a similar outward recessed extension could be provided here, removing the cross-member portion of 214 that spans the connection points of lower lip protecting member 232 such that first and second portions 214a and 214b of the lower anterior connecting member 214 connect only to the connection points of the lower lip protecting member 232, thereby providing an additional flex or relief point. In other words, first and second portions 214a and 214b may not run generally horizontally, continuously between the anterior regions of lower side members 210a and 210b, but may include a forward extension and recess analogous to recess 205a in the upper frame portion.

As with device 100, a posterior width 220 of upper 204 and lower 206 frame portions as defined between posterior regions 216 may be greater than upper anterior width 222 and/or lower anterior width 222' of the upper 204 and lower 206 frame portions, respectively. Such relationships may be as described previously in the context of device 100, where posterior width 220 is greater than upper anterior width 222, and upper anterior width 222 is greater than lower anterior width 222'. Also similar to device 100, frame 202 may also include a posterior crossbar 224 extending between posterior regions 216*a* and 216*b*. Because of the greater posterior width, the side members 208*a*, 210*a*, and 208*b*, 210*b* from posterior ends 216, anteriorly forward, may be angled inwardly, towards the centrally disposed lip protecting members.

Figure 8:
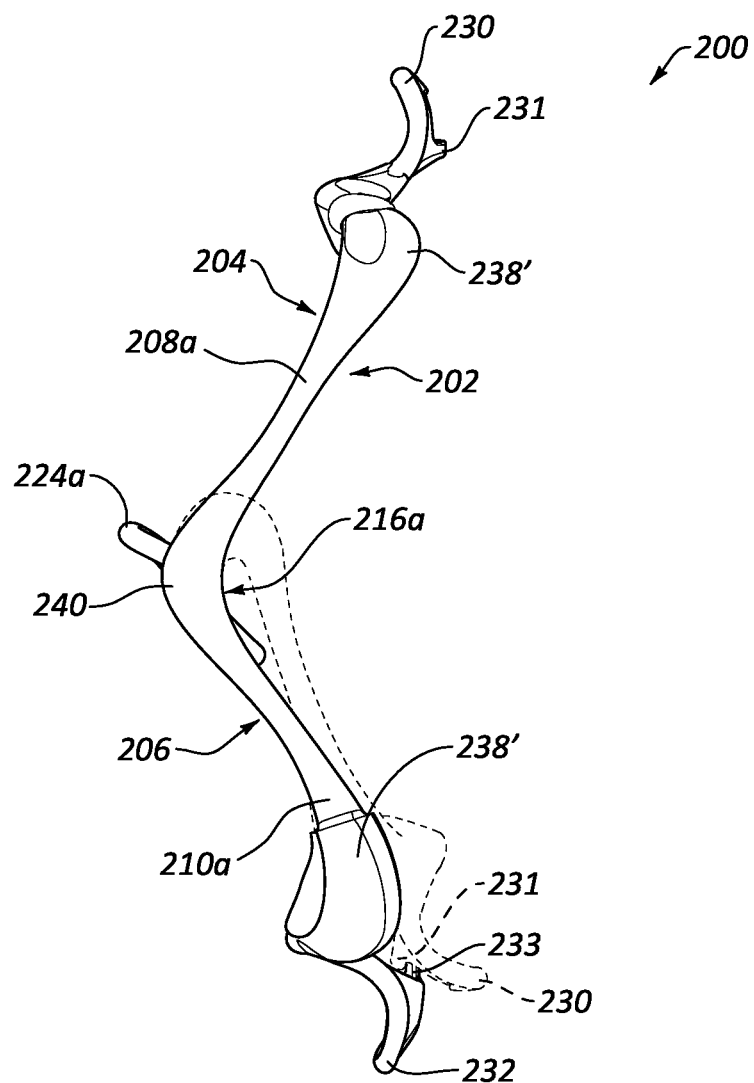
FIG. 8 is a side view of the cheek and lip expansion device of FIG. 6, with the upper frame portion also shown in broken lines indicating how it may be folded and latched with the lower frame portion.
Figure 9:
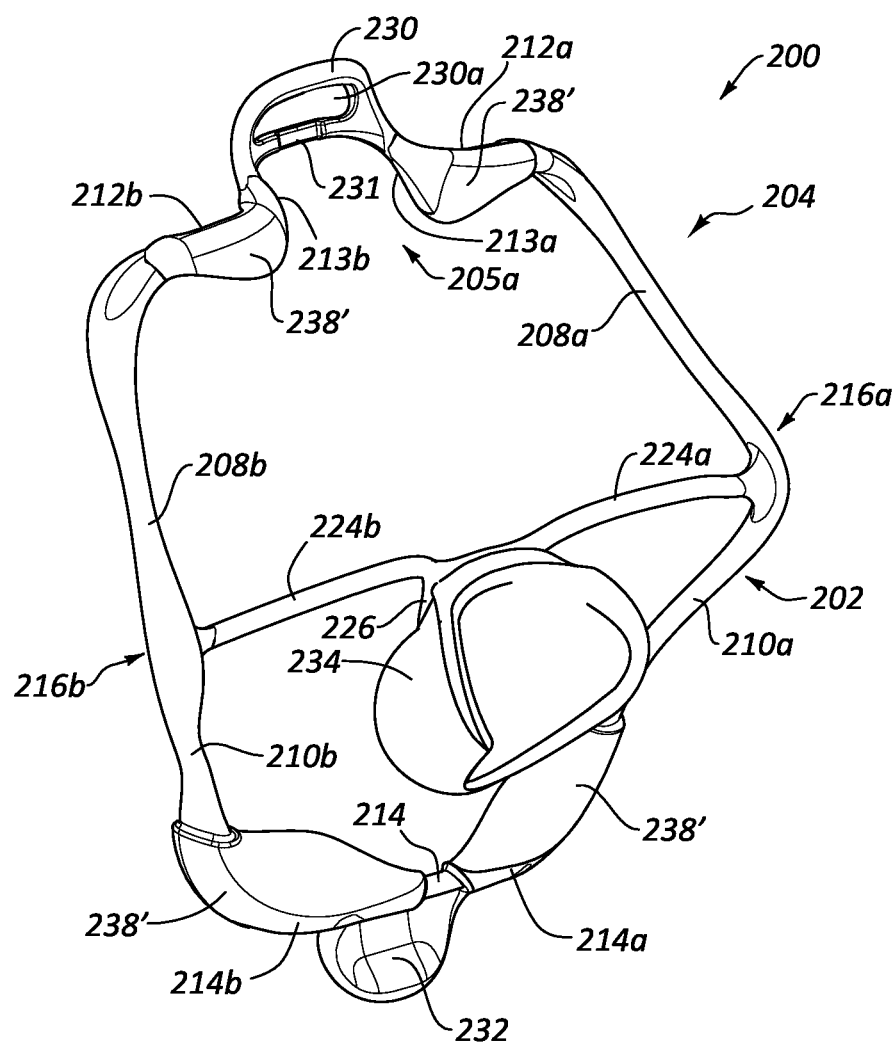
FIG. 9 is a posterior or rear perspective view of the cheek and lip expansion device of FIG. 6.

Illustrated upper and lower lip protecting members 230 and 232 are also somewhat different than those illustrated with device 100. Both members 230, 232 may include a hollow portion 230*a*, 232*a*, respectively. Upper lip protecting member 230 may include a cross-member 231 adjacent portion 230*a*, which cross-member 231 may serve to latch with a corresponding latch member 233 of lower lip protecting member 232. In addition, the upper lip protecting member 230, particularly as it is extended upward due to extensions 213, may act as a flex or relief point at which the various portions of the upper frame (e.g., upper anterior connecting member portions 212*a*, 212*b*, lip protecting member 230, etc.) may begin to arc or bend to provide increased compliance and resiliency. As with device 100, lip protecting members 230 and 232 may curve over and protect the patient's lips during a dental procedure, extending outside the patient's mouth. Because of their extension outside of the mouth, they provide a convenient handle that can be gripped when removing or positioning the device. FIGS. 8 and 13C-14B show the lip protecting members 230 and 232 selectively engaged with one another, with cross-member 231 latched with latch member 233. For example, cross-member 231 may snap or compression fit under latch member 233, holding cross-member 231, and thus upper frame portion 204 latched to lower frame portion 206. Tongue guard 234 is not shown in FIG. 8 so as to more clearly show the other structures. As seen in FIG. 8, the side view of the expanded expansion device may be generally L-shaped, as defined by the upper and lower frame portions.

Instead of floating gussets 128, posterior crossbar 224 of device 200 may be connected directly to the posterior ends of side members 208 and 210, e.g., at the location of joints or posterior arced regions 216. Posterior crossbar 224 may include a curved, bowed, v-shaped or u-shaped anteriorly curved portion 226 (e.g., centrally located along crossbar 224) to facilitate side-to-side collapsibility of device 200. As shown, a cross-member portion 227 of crossbar 224 may extend between the ends of v-shaped or u-shaped portion 226 (e.g., providing a triangular shaped portion in crossbar 224). The anteriorly curved portion 226 and the cross-member portion 227 may also aid in removably attaching a tongue guard 234, as shown. In some embodiments, the crossbar 224 may include first and second posteriorly curved portions 224*a*, 224*b*, which may be provided on either side of curved portion 226, if present, e.g., with first curved portion 224*a* between posterior end 216*a* and centrally disposed curved portion 226, and second curved portion 224*b* between posterior end 216*b* and centrally disposed curved portion 226.

Figure 11:
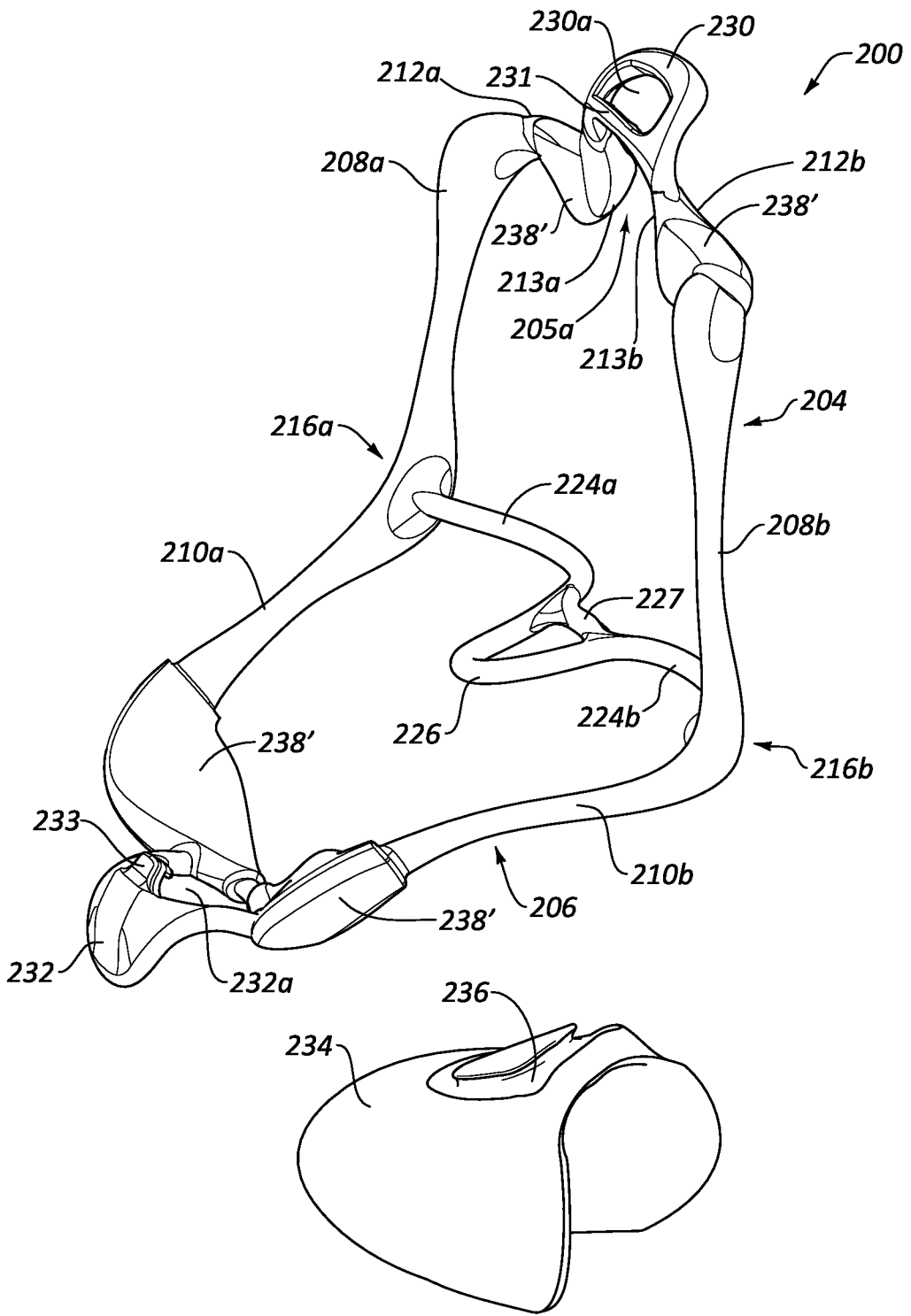
FIG. 11 is a perspective view of the cheek and lip expansion device of FIG. 6, with the tongue guard shown separated from the cheek expansion device.
Figure 12A:
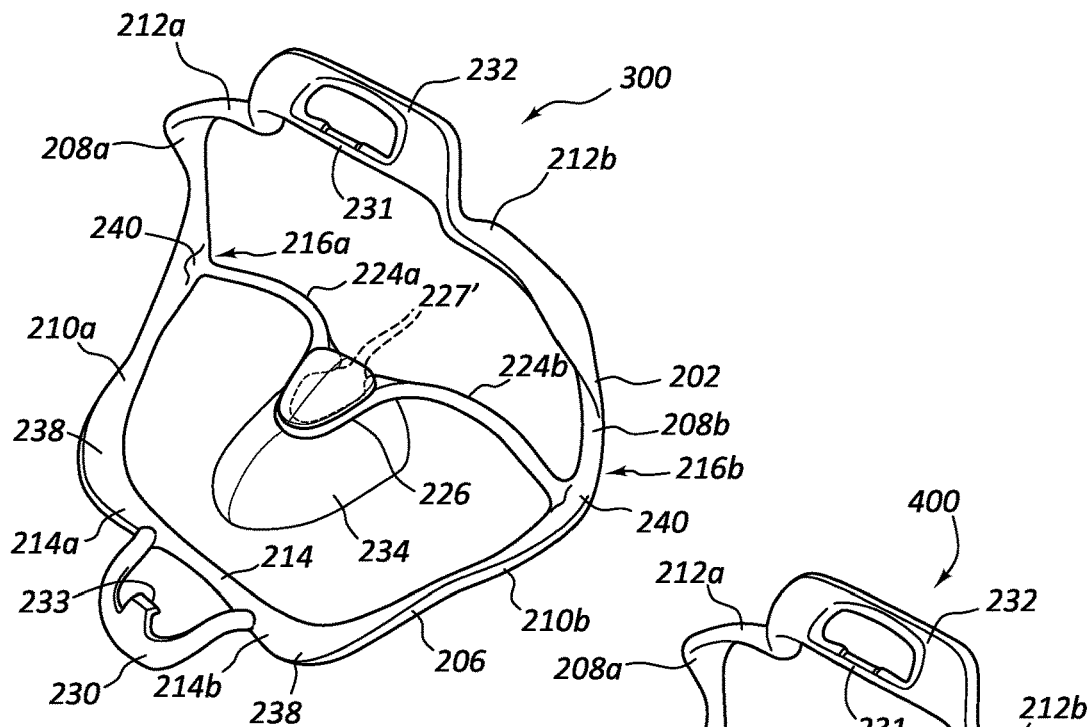
FIG. 12A is a front perspective view of another exemplary expanded cheek and lip expansion device.
Figure 18A:
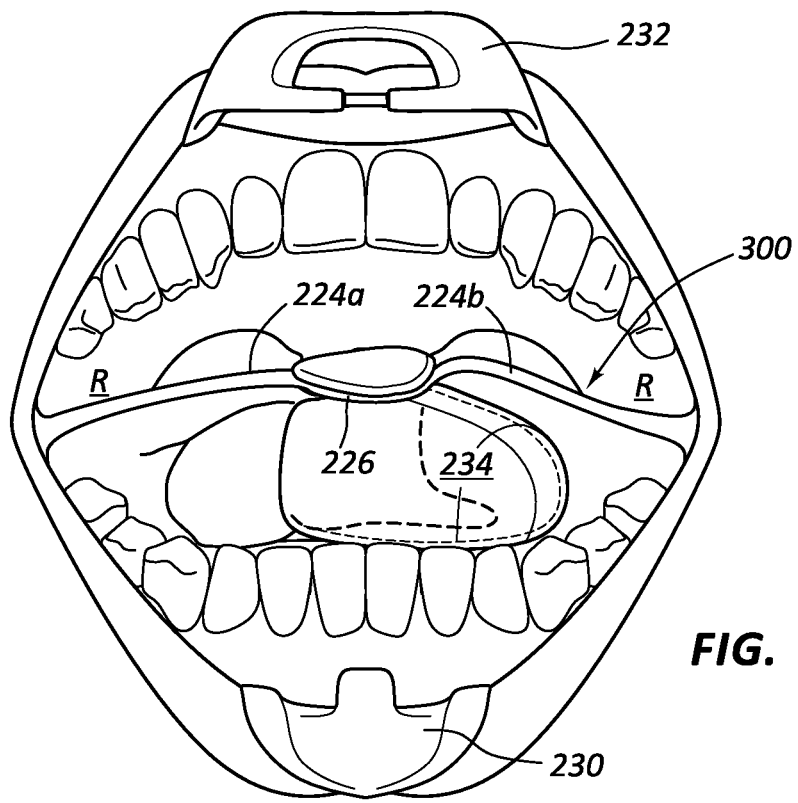
FIGS. 18A-18D show how with the cheek and lip expansion device in the mouth and the distal tip of the patient's tongue in the tongue guard, the patient is able to still move their tongue to either side, up, and down.
Figure 18B:
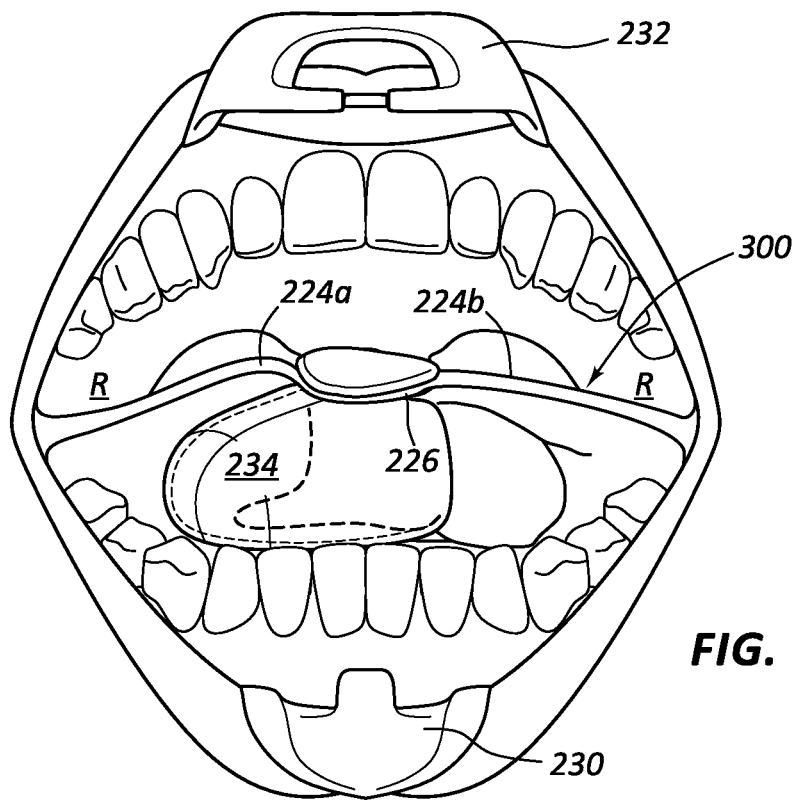
Figure 18C:
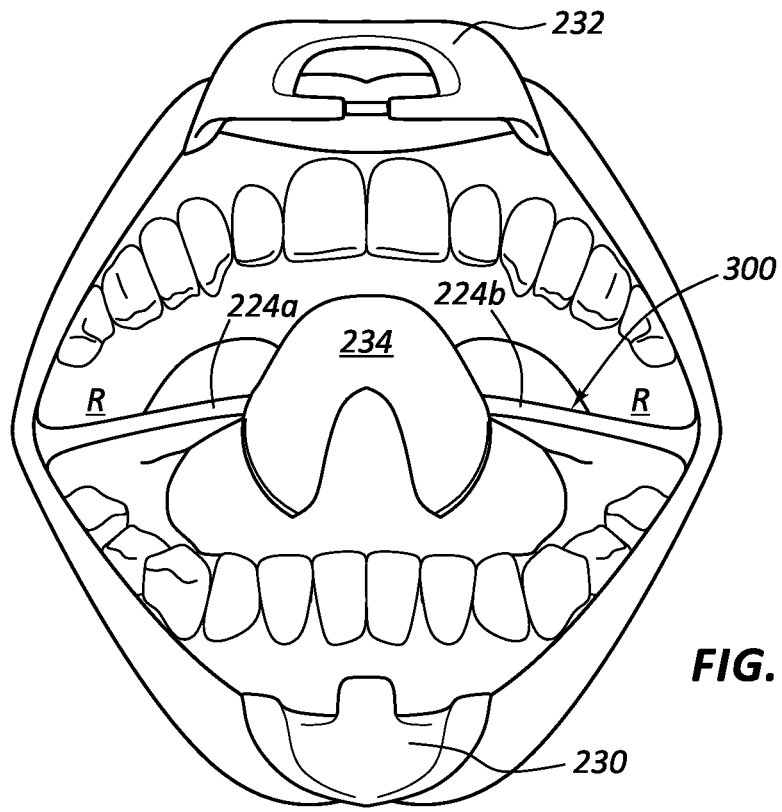

Tongue guard 234 is shown as differently configured than tongue guard 134 of device 100. Tongue guard 234, may be selectively removable (e.g., via a snap-fit compression-fit, or similar, as shown (e.g., FIG. 11 shows the tongue guard 234 detached). For example, a top surface of tongue guard 234 may include a recess 236 corresponding to curved portion 226, allowing curved portion 226 to snap into recess 236, attaching tongue guard 234 to posterior crossbar 224, within centrally disposed anteriorly curved portion 226. The expansion device 300 seen in FIG. 12A is similar to expansion device 200, but without the cross member portion 227 that extends fully across the rear of anteriorly curved central portion 226. Rather, expansion device 300 includes a retention feature such as retention protrusions 227', which allows tongue guard 234 to be pressed into place from the rear of curved portion 226, and retention protrusions 227' flex to allow receipt of the tongue guard therein, and then spring back, retaining the tongue guard in place. Without such protrusions, the tongue guard may be more likely to fall out. For example, retention protrusions 227' may extend inwardly from opposite sides of first and second curved members 224*a*, 224*b*, or from oppositely inwardly oriented sides of anteriorly curved portion 226. Tongue guard 234 may be configured as a sheath, which may be closed at the anterior end, closed along the top, and open at the posterior end, so that the tongue may be introduced therein. The bottom end may also be largely open (see FIGS. 9 and 18C). As such, structure 234 may serve as a garage into which the tongue may be introduced, so as to ensure the tongue does not interfere with practitioner access to the desired areas of the oral cavity, while also protecting the top distal end of the tongue as it is enveloped by guard 234.

When the patient's tongue is received within guard 234, the naturally applied force may push the expansion device 200 forward (e.g., 1-4 mm), causing a further expansion of expansion device 200 within the oral cavity, to create an even greater clearance around the dental arches (i.e., between the dental arches and the cheeks and/or lips, as well as between the tongue (tongue guard 234) and the lingual dental arch surfaces). Such forwardly applied force may work in conjunction with posterior loading of the device, e.g., as provided by loading of the crossbar 224 against the soft tissue covering the mandibular ramus and/or by loading of the posterior ends 216 on the backwall of the vestibule. Such abutment and loading of the frame relative to the mandibular ramus and posterior tissue of the oral cavity may result in increased three-dimensional inflation of the cheeks and lips in x-axis (side-to-side), y-axis (top-to-bottom), and particularly z-axis (forward) dimensions.

Figure 10A:
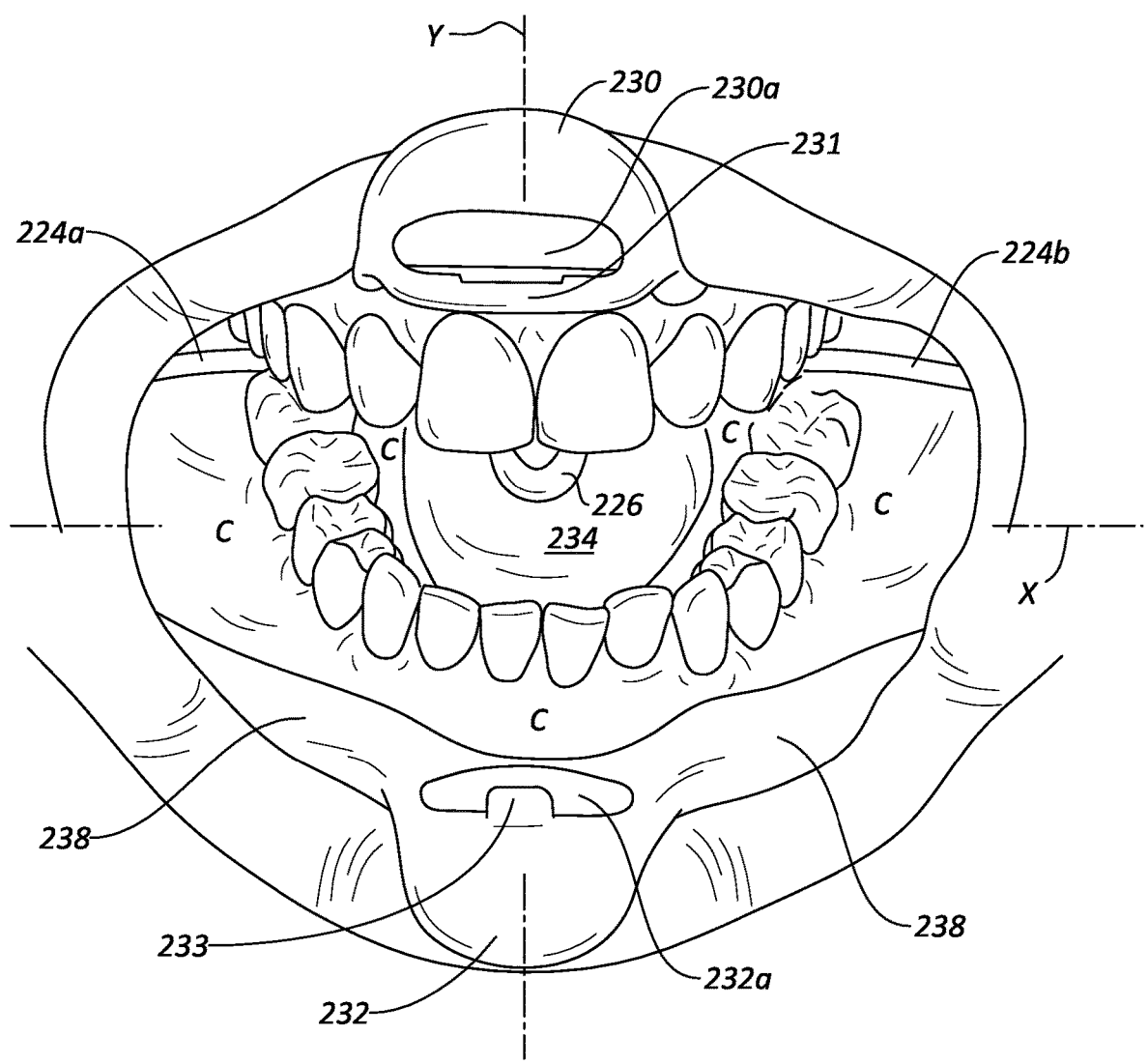
FIG. 10A is an anterior or front view of the cheek and lip expansion device of FIG. 6 installed within the oral cavity of a patient.
Figure 17A:
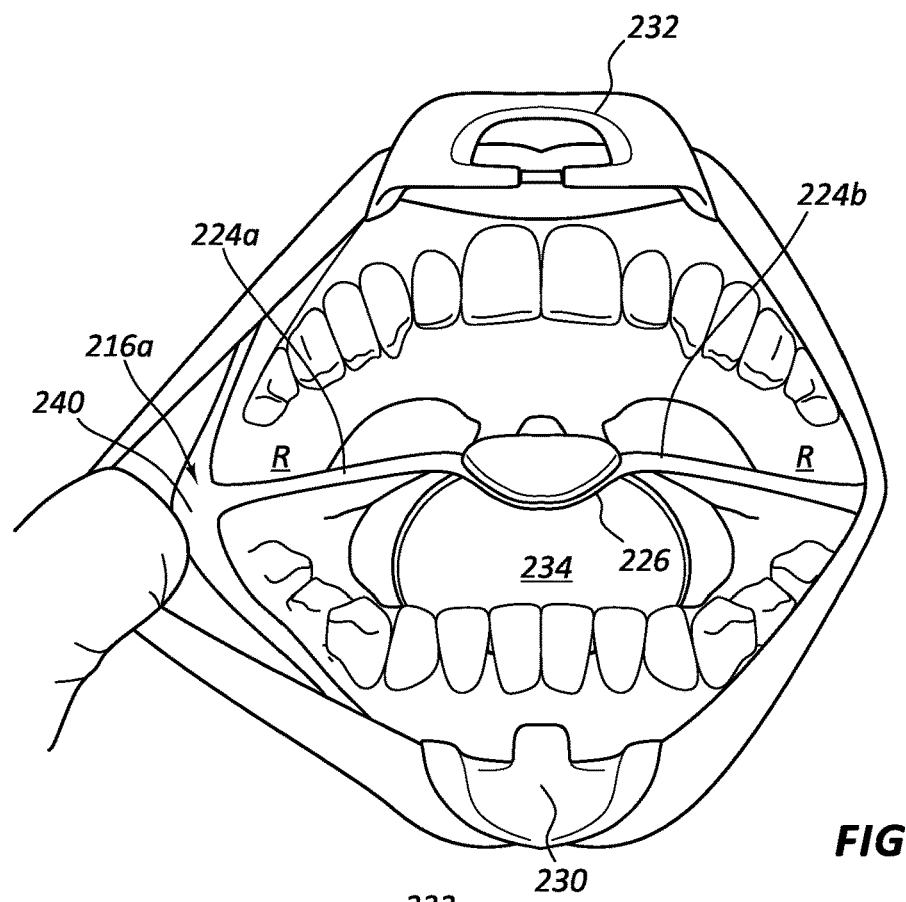
FIGS. 17A and 17B illustrate how, with the cheek and lip expansion device in the mouth, the lips are not fully stretched side-to-side around the mouth, which permits asymmetric deformation of the person's lips to one side or the other without excessively stretching the lips and causing pain to the patient.
Figure 17B:
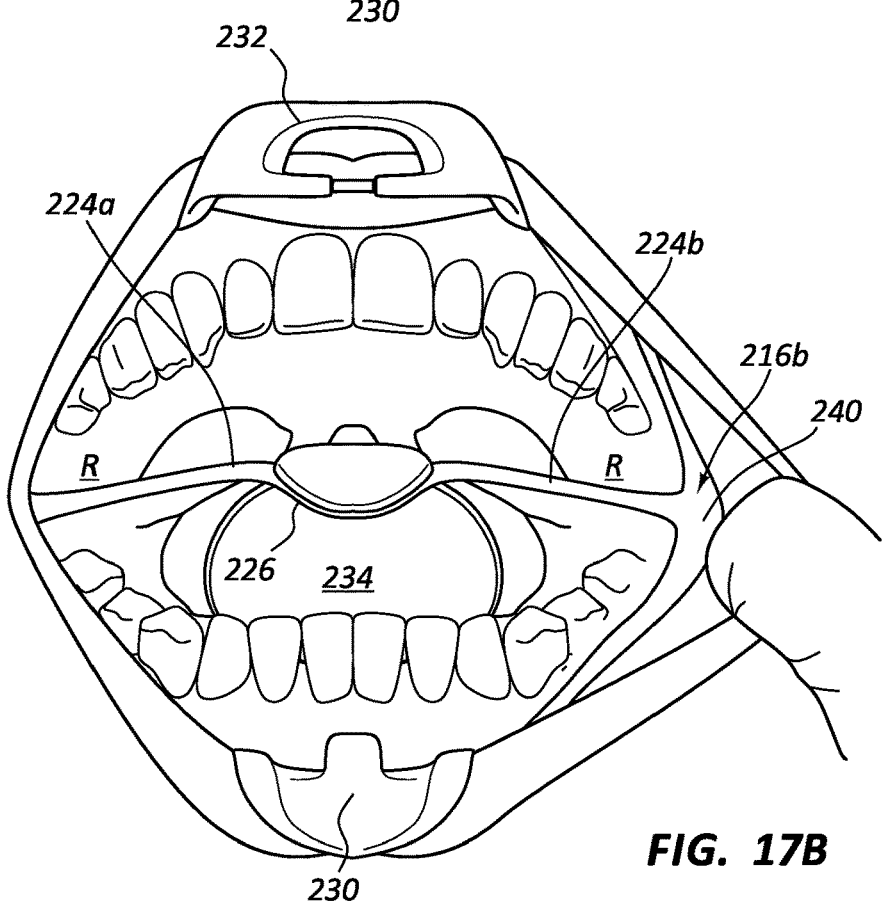

Clearance provided between the dental arch and the soft tissue of the cheeks and/or lips with the device in place may depend on the particular anatomy of a given patient, but may typically be as much as 2 cm, e.g., at least about 4 mm, at least about 8 mm, at least about 12 mm, etc. FIG. 10A shows a typical clearance (C) in the lower vestibule, around the entire buccal side of the lower dental arch of 4 mm to about 2 cm, also showing good clearance on the lingual side of the lower dental arch, between the tongue guard 234 and the dental arch. As seen, the device is able to retract both the lips and the cheeks away from the dental arch, providing excellent clearance all around. All of this is advantageously accomplished without expanding the lips side-to-side to an extent that would be uncomfortable to the patient, as is often provided by other existing cheek or lip retractor devices. Rather, much of the retraction or expansion is achieved by pushing the lips forward, and the cheeks outwardly, rather than simply opening the mouth, and stretching the lips side-to-side as far as possible as in many prior retraction devices. Because of this difference, it is possible for the practitioner to asymmetrically pull one cheek or the other to one side or the other, for a wider working field on a given side, as shown in FIGS. 17A-17B. While shown with use of a tongue guard, of course, any of the devices according to the present invention may be employed with or without a tongue guard.

Figure 10B:
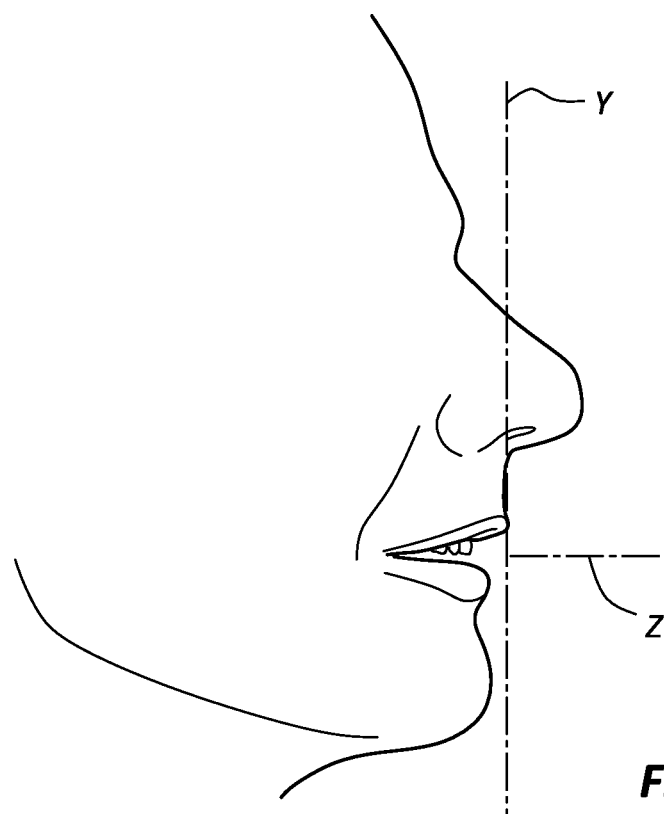
FIG. 10B-10C are side profile views showing the patient's mouth without the expansion device installed (FIG. 10B) and with the expansion device installed and expanded (FIG. 10C), showing how the upper and lower lips are inflated, displaced and flared forward, in the z-axis direction.
Figure 10C:
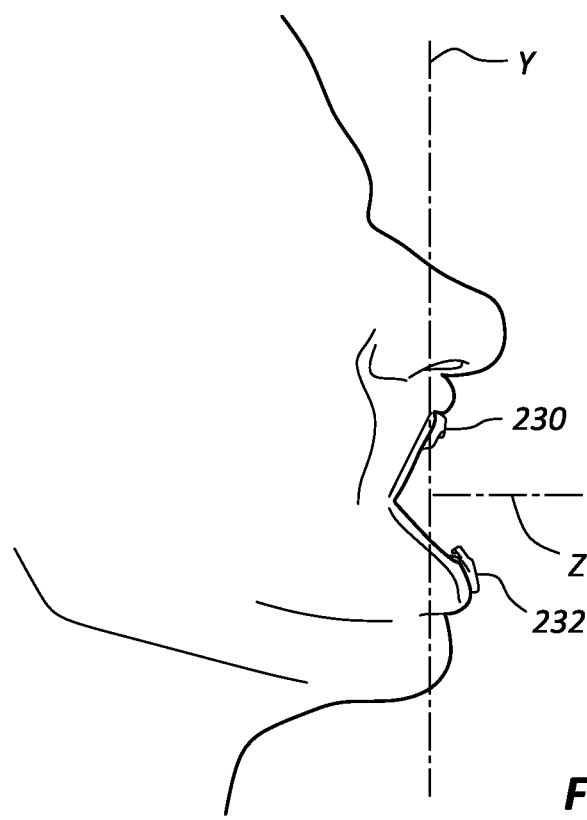

FIGS. 10B and 10C show the side profile of the patient, both before (FIG. 10B) and after (FIG. 10C) installation and expansion of the device. FIG. 10C shows how the upper and lower lips of the patient are flared and inflated forward, in the z-axis direction upon expansion of device 200. The clearance C thus provided in the z-axis direction, between the upper lip and the upper dental arch is provided as the upper anterior connecting member 212 resides within the upper anterior vestibule, and the frame 202 is posteriorly loaded. For example, the posterior arced regions 216 may abut against the backwall of the facial vestibules, and portions 224a and 224b of posterior crossbar 224 may abut against the soft tissue over the ramus, pushing the expansion device 200 forward, so that upper anterior connecting member inflates, displaces, and flares the upper lip further away from the upper dental arch than would otherwise be the case. Similarly, the lower anterior connecting member 214 resides within the lower anterior vestibule, and the same posterior loading described above similarly results in inflation and flaring of the lower lip forward, in the z-axis direction, away from the lower dental arch. Because of the anatomical differences described above in reference to the length of the upper side members 208 relative to the lower side members 210 (i.e., longer upper side members), in at least some embodiments, the upper lip may be flared out further than the flaring ($\Delta z$) provided to the lower lip. Of course, the lower lip may also be flared out further, depending on the specific geometry of the expansion device. As seen in FIG. 10C, as the expansion device 200 may also default the patient's jaw to an open position (due to the resilient top to bottom opening or loading force provided between the upper and lower frame portions 204, 206 in the expanded configuration), the upper and lower lips may also be directed upwards and downwards, respectively, (in the y-dimension).

As will be apparent from FIGS. 10A-10C, when installed, the expansion device pushes out on the lips and the cheeks simultaneously, retracting these soft tissues away from the dental arches. In that configuration, particularly when employed with a tongue guard such as guard 234, the device "floats" within the mouth, acting as a tent or umbrella frame to expand the lips and cheeks (which are the "web"). The posterior crossbar 224 and/or posterior ends 216 may engage soft tissue covering the mandibular ramus, further pushing the device forward, as it "floats" within the mouth. Because of its "floating" and posteriorly loaded configuration, the posterior loading (which may be enhanced by the person pressing the tongue forward in guard 234) can shift the device as a whole forward (e.g., 1-4 mm) in the z-axis direction, creating significantly more useful retraction of the cheeks and lips, as compared to existing devices, which are not configured to provide such posterior loading, and forward, z-axis inflation and flaring.

The described expansion devices also provide improved retraction or expansion adjacent the posterior regions of the dental arch, providing excellent clearance all around the dental arch, including the rear molars (e.g., the $2^{nd}$ molars) or other posterior teeth, without the device blocking or impeding practitioner access to these areas around the posterior teeth. In addition, there is no need for an anterior continuous ring that circles the opening of the mouth, which can interfere with access to the cuspids and bicuspids. For example, such a ring present in the anterior portions of the oral cavity, between the cheeks or lips and the teeth, necessarily cross from the upper to lower vestibules or other portions of the mouth. Because such crossing occurs in the anterior region of the mouth (e.g., near the cuspids and/or bicuspids), it places frame structure where it interferes with the ability to access these tooth positions. The upper and lower frame portions of the present expansion devices rather run anteriorly-posteriorly, within the vestibule, and thus can avoid crossing from upper to lower regions of the mouth (and thus crossing over some tooth positions). Rather, no such upper to lower crossing occurs in the vicinity of the dental arches, but occurs only behind the dental arches, at posterior ends 216.

Returning to FIG. 6, one or more bumper covers 238' may be provided over enlarged, thickened corner bumpers on frame 202. While the anterior thickened corner bumpers on frame 202 are covered so as to not be visible in FIGS. 6-11, they may be similar or identical to anterior corner bumpers 138 seen in FIGS. 1-5, or those (238) of FIGS. 12A-16A. Such underlying thickened corner bumpers provide increased surface area for overmolding or otherwise bonding of softer, bumper covers 238' thereover. In an embodiment, such bumper covers 238' may comprise a different material than adjacent frame 202, e.g., comprising a softer, flexible, and/or elastomeric material overmolded with respect to frame 202. For example, bumper covers 238' may have a Shore A durometer in a range from 0 to about 50, from 0 to about 25, or about 15. Tongue guard 234 may similarly be formed of a different material than frame 202, and may have durometer characteristics that are harder than bumper covers 238'. For example, tongue guard 234 may have a Shore A durometer hardness in a range from about 50 to about 100, from about 50 to about 90, or from about 60 to about 80. The tongue guard may comprise a material having greater flexibility and/or elasticity than the flexible spring-like frame.

Any device according to the present invention may advantageously allow full closure of the patient's mouth, with the device installed, as seen in FIGS. 17A-17B. This is a distinct advantage over many existing cheek or lip retractor devices, where full closure of the jaw is not possible. Because closure of the jaw is possible, a practitioner may perform a bite-check without having to remove the device. As illustrated in FIGS. 10A-10C, the devices 100 and 200 provide excellent displacement, retraction or expansion of both the lips and the cheeks, so as to provide a large clearance area (C) around the teeth where the practitioner would like to access, yet without stretching the lips in a side-to-side dimension to their limit. Such clearance provides excellent results for introduction of a dental drill, or for use with an intra-oral scanner, for example, to scan the dental and/or oral structures within the mouth (e.g., for digital crown manufacture). Another advantageous use of the expansion device may be for in-office tooth bleaching. Because the device provides such excellent clearance around the dental arches (i.e., between the dental arch and adjacent soft tissue cheeks and lips), there is less risk of contact between irritative tooth bleaching compositions and such soft tissues, which may otherwise irritate or burn the soft tissues.

In addition to allowing full closure of the jaw, the expansion devices according to the present invention may be configured so as to not block or impede practitioner access to the posterior teeth of a patient. For example, this may typically include bicuspids in children, or first and second molars (or even third molars) in adults. This is advantageous, as some retraction devices do not provide good access to the posterior teeth, particularly the rear molars. For example, the side members (e.g., 208 and 210) and posterior crossbar (224) may tend to extend bucally, and generally parallel to, and then wrap around the dental arch, behind the rear molars. The crossbar 224 may reside in a retromolar region, e.g., between the ramus and the molars. In addition, as described above, the inclusion of thickened corner bumpers (e.g., 138, 238) within the anterior corners of the frame allows these thickened portions to reside within the anterior corners of the patient's vestibule, aiding in flaring the lips forward, and reducing any tendency of the device to uncomfortably "grab" or "jab" the corners of the mouth of the patient.

According to an embodiment, the frame of any of the embodiments may typically be formed from a polymeric material. For example, the frame may be injection molded or otherwise formed a thermoplastic or other suitable polymer material (e.g., all as a single piece of material). In another embodiment, the frame may be formed of a shape-memory nickel-titanium alloy exhibiting a martensitic transformation temperature between ambient temperature (e.g., about 20° C.) and body temperature (e.g., 37° C.). Such a shape memory alloy could allow the expansion device to be highly deformable at ambient temperature prior to and during insertion, while become rigid as it warms to body temperature. This would be advantageous in practice because the alloy could be flexible and easily deformed before insertion, while still providing excellent retraction after warming up to body temperature. Inexpensively manufactured polymeric expansion devices may be intended for single use, so as to be disposed of after a single use. Plastic materials exhibiting sufficient flexibility for the frame have been found to provide excellent results. The flexibility may result from the geometry, e.g., the thinness of at least some portions of the various elongate members. For example, side members 208 and 210 include thinner central portions between their thickened posterior ends 240 and their thickened anterior ends 238, allowing the members to flex and bend as needed for collapsibility. The posterior crossbar 224 is similarly flexible due to its geometry, including the thinness of the crossbar, and the variously curved portions (e.g., 224a, 224b, and 226). In any case, the frame and its material is sufficiently flexible so as to allow flexing of the upper and lower frame portions towards one another, as well as flexing of the left and right sides towards one another. When released, the frame is able to recoil back to an expanded configuration. Some models, such as one formed of a shape memory nickel-titanium alloy, may be autoclaved or otherwise sanitized following use, so as to allow reuse of the device.

A device in which the frame is formed of a shape memory nickel-titanium alloy may further include an exterior coating (e.g., silicone, any suitable overmolded plastic, or other coating otherwise encapsulating the Ni—Ti frame) to retard (e.g., insulate) the temperature induced phase transformation of the nickel-titanium alloy. Such a coating may control the rate of heating of the frame after insertion, allowing retraction or expansion to occur at a gradual, comfortable and gentle pace.

Figure 12B:
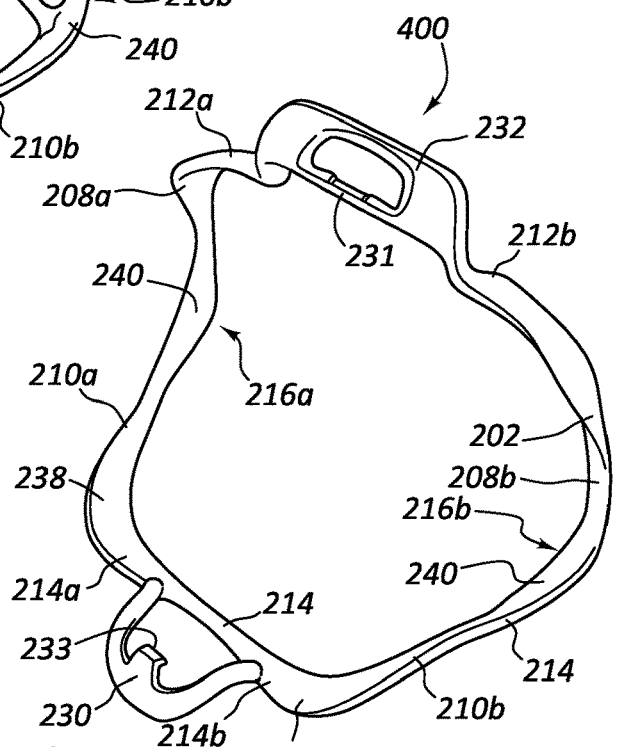
FIG. 12B is a front perspective view of a cheek and lip expansion device similar to that of FIG. 12A, but without any posterior crossbar.
Figure 12C:
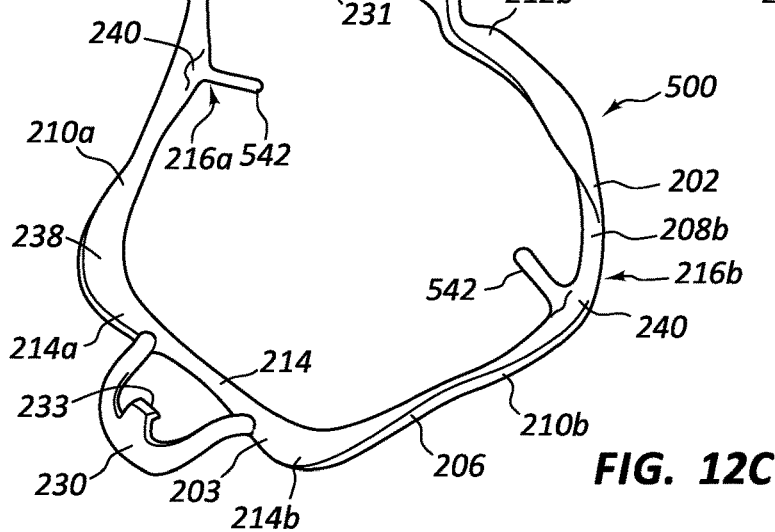
FIG. 12C is a front perspective view of a cheek and lip expansion device similar to that of FIG. 12A, without the posterior crossbar connecting posterior regions of the first and second upper and lower side members, but still including inwardly protruding extensions (e.g., a portion of the crossbar), to aid in loading the device against soft tissue covering the mandibular ramus.

FIGS. 12A-12C show further exemplary cheek and lip expansion devices according to the present invention. FIG. 12A shows a device 300 similar to device 200, but without the bumper covers 238', and without a continuous cross-member 227 spanning central anteriorly curved portion 226. Device 300 includes a flexible spring-like frame 202, including an upper frame portion 204 and a lower frame portion 206 which are flexible and resilient so as to selectively assume collapsed and expanded configurations during installation and use. As with device 200, both upper and lower frame portions 204 and 206 include upper side members 208 and lower side members 210. Upper anterior connecting member 212 joins together the anterior portions or ends of the first and second upper side members 208a and 208b. Lower anterior connecting member 214 joins together and extends between the anterior portions or ends of the first and second lower side members 210a and 210b. The posterior regions of the first upper and lower side members 208a, 210a are joined at posterior arced region 216a, while the posterior regions of the second upper and lower side members 208b, 210b are joined at posterior arced region 216b. Posterior regions 216 form flexible yet sufficiently rigid joints that resist bending at a single point, but rather distribute the bending moment along a substantial length of the upper and lower side members 208, 210 during collapse along the y-axis. Distribution of the bending or flexing forces associated with top to bottom collapse of the expansion device is aided by providing the posterior ends of side members 208 and 210, where they join (at posterior regions 216) with a thickened structure 240, so that the thickened cross-section at the posterior regions 216a, 216b resist bending, forcing the bending to occur more anteriorly along the upper and lower frame portions (where the side members are thinner). As a result, when bending, little to no actual bending or flexing may occur within the region of posterior arced regions 216a, 216b, as seen in FIGS. 13A-13C. Such a configuration prevents posterior arced regions (also referred to herein as joints) 216a, 216b from becoming increasingly acute, and jabbing into the backwall of the vestibule during insertion or use, providing greatly increased comfort.

As seen in FIG. 12A (also particularly apparent in FIGS. 1-5), the upper and lower frame portions of the device may include distinct anterior corners, which are defined by a relatively tight radius of curvature across bumpers 138, 238, at the corners. For example, the radius of curvature across bumpers 138 or 238 may be in a range of about 8 to about 22 mm, about 10 to about 20 mm, or about 15 mm. The upper and lower frame portions are not simply rounded, e.g., with an oval or circular configuration, or defined by a generally constant radius of curvature over a significant portion of their length. As shown in FIG. 12A and FIGS. 1-5, the side members on either side of the upper and lower frame portions may be relatively straight from the thickened posterior regions 216 towards the forward (anterior) direction, towards the relatively tightly curved corners at anterior bumpers 138 or 238. Such tightly curved corners 138, 238 (e.g., they could be termed "squared corners") conform to the anatomical shape of the upper and lower anterior vestibules between the dental arch, gums and the person's lips. The upper anterior corner bumpers 138, 238 may also angle or flare downwardly and outwardly across the thickened section, while the lower anterior corner bumpers 138, 238 may similarly angle or flare upwardly and outwardly. This is perhaps best seen in the corner bumpers of FIGS. 2 and 13C. Such configurations ensure that the frame does not contact or irritate the canine prominence of a patient. Such shape and contouring provides increased comfort to the patient.

Because of anatomical differences in the length of the upper and lower dental arches and associated vestibules, the two upper corner thickened bumpers 138, 238 of the upper frame portion may be further apart from one another as compared to the two lower corner bumpers 138, 238 of the lower frame portion. As described relative to the anterior width of the upper and lower frame portions, the upper frame anterior width 122 may be greater than the lower frame anterior width 122' (see FIGS. 1, 2, and 6). Where the corner thickened bumpers 138, 238 are positioned at the ends of the anterior width (i.e., the intersection between the side members and the corresponding upper or lower anterior connecting members), the distance between such corner thickened bumpers also differs from upper to lower, with the upper corner thickened bumpers 138, 238 being further apart from one another than the lower corner thickened bumpers 138, 238. Such a difference anatomically conforms to differences in sizes of the upper and lower dental arches, and the upper and lower anterior vestibules. This difference may also cause the upper lip to flare out further (in the forward, z-direction) than flaring of the lower lip. For example, the upper lip may actually be forward of the lower lip, or the Δz difference provided by the expanded device may exhibit a greater Δz in the upper lip than the lower lip (i.e., difference in positions of the upper lip due to the expanded device may be greater than the difference in lip positions of the lower lip, due to the expanded device).

Also for anatomical reasons, the upper corner thickened bumpers 138, 238 may be more rounded, and enlarged as compared to the two lower corner thickened bumpers 138, 238. Larger, upper corner bumpers also aids in ensuring that the upper lip is flared out further than the lower lip. As described herein, one or both of the upper or lower corner thickened bumpers 138, 238 may include a bumper cover (e.g., 238' of FIGS. 6-9 and 11) comprising a material with greater softness, greater flexibility, and/or greater elasticity than the underlying bumpers of the frame. Such cushioning bumper covers 238' may provide a comfortable elastic cushion between the upper and lower gums and lips. FIGS. 12A-16A do not show any bumper covers, in order to better show the underlying frame geometry, particularly bumpers 238 that such covers may be bonded to or otherwise attached to.

Device 300 is further shown as including a posterior crossbar 224 interconnecting the posterior arced regions 216 of the first and second upper and lower side members 208 and 210. As described, crossbar 224 may be configured, in combination with a mandibular ramus, to effect posterior loading of the flexible, resilient frame 202, which posterior loading assists in flaring the cheeks and lips outward, forward, and open (i.e., in x, y, and z-axis directions).

As shown in FIG. 12A and described previously, the posterior crossbar 224 may include first and second curved members 224a and 224b which are posteriorly curved (i.e., curved backwards), so as to represent the most posteriorly disposed portions of the expansion device (e.g., see the side views of FIGS. 3 and 8). The posteriorly curved members 224a, 224b may be joined at essentially a middle portion of the crossbar 224, near anteriorly curved portion 226. Crossbar 224 may thus include three curves (e.g., two posteriorly curved portions 224a and 224b, and an anteriorly curved portion 226 or other middle flexure feature). Because of the posterior curvature of members 224a, 224b, these posteriorly curved portions can load against the soft tissue covering mandibular ramus of the patient, so that the ramus applies posterior loading to the device through crossbar 224, pushing the device 300 forward. Such posterior loading further flares the lips of the patient forward, increasing the working field available within the mouth, particularly adjacent the lips. Curved members 224a, 224b may also facilitate the collapsed insertion configuration of the frame, where the frame is collapsible from side-to-side upon application of a side-to-side collapsing force, as well as facilitating the expanded configuration of the frame, where the frame is outwardly expanded by opening up from side-to-side as the collapsing force is released. Posteriorly curved members 224a, 224b may also aid in preventing stimulation of the gag reflex of the patient.

Rather than continuous cross-member 227 across the rear of anteriorly curved portion 226, the configuration of FIG. 12A shows retention protrusions 227', which aid in retaining tongue guard 234 in place, while also allowing its insertion from behind. In addition, by removing the continuous cross-member 227 (and even with retention protrusions 227'), the ease of collapsing the frame from side-to-side is improved.

FIG. 12B illustrates another device 400 also similar to device 200, but without the crossbar 224. Even without such a crossbar, the posterior ends 216 have been found by the inventors to provide for at least some degree of posterior loading of the device as the posterior ends 216 bear against the backwall of the vestibule of the patient. FIG. 12C illustrates another device 500 similar to devices 200, 300, and 400, but in which most of the posterior crossbar 224 has been removed. Device 500 instead provides inwardly protruding extensions 546 on posterior arced regions or joints 216a, 216b. Such elongate extensions may be sufficient in length (e.g., 0.25 inch to 1 inch in length) to still provide posterior loading of extensions 542 on the mandibular ramus of the patient, without providing a continuous crossbar between posterior arced regions 216. Where such extensions are provided, they may be rounded at their free ends for comfort. It will be apparent than in devices 400 and 500, no tongue guard may be provided.

In an embodiment, the posterior crossbar 224 may be selectively removable from the remainder of frame 202. For example, the crossbar could be configured as a tube that fits over projections such as projections 542 seen in device 500, or a ball and socket joint could be provided at each end (e.g., at joints 216), or any other suitable connection mechanism (e.g., press-fit, friction fit, snap fit, etc.) could be provided. If desired, a practitioner could convert the configuration seen in FIG. 12A to that of 12B or 12C by simply cutting or otherwise removing some portion or all of the crossbar 224.

III. Exemplary Methods of Placement and Use

FIGS. 13A-17B illustrate various aspects associated with placement and use of the cheek and lip expansion devices. For example, FIGS. 13A-13C show how the device 300 may be collapsed from top to bottom. FIG. 13A shows partial collapse as compared to the expanded state seen in FIG. 12A, while FIG. 13B shows progressively further top to bottom collapse, and FIG. 13C shows device 300 collapsed top to bottom to the degree that the latch member 233 can be engaged with cross-member 231. As shown, (e.g., see FIG. 13B), the cross-member 231 may include a recess formed into the posterior surface of the cross-member, into which latch member 233 is received, latching the upper and lower frame portions 204, 206 to one another.

A comparison of FIG. 12A with FIGS. 13A-13C show how the upper and lower side members (e.g., 208a and 210a on a first side and 208b and 210b on a second side) are joined at their posterior ends to form first and second bendable radii about arced regions 216, which resist bending at a distinct point so as to spread the bending forces out away from regions 216, towards the other portions of the side members 208 and 210. For example, because of the thickening 240 at posterior regions 216, little to no bending may actually occur at this posterior location, while the majority of the bending may occur along the thinnest regions of the side members (e.g., between thickened bumpers 238 and thickened posterior ends 240). Other mechanisms could alternatively be employed to similarly resist bending at a desired distinct location (e.g., use of a different material, etc.).

FIG. 13C also perhaps best illustrates how the thickened corner anterior bumpers 238 of both the upper and lower frame portions may also be anatomically angled, so as to more comfortably fit within the upper and lower corners of the anterior vestibule. Specifically, the lower bumper is shown as angling upward and outward, and the upper bumper as angling downward and outward. For example, as labeled on the left side in FIG. 13C, the lower corner bumper 238 may include outside and inside angled surfaces 348 and 350, respectively. Such angles match the anatomy of the corners of the vestibule into which lower bumper 238 is to be received. Similarly, the upper corner bumper 238 is shown as including outside and inside angled surfaces 352 and 354, respectively, which angles match the anatomy of the corners of the vestibule into which the upper bumper 238 is to be received. For example, the lower outside angle 348 may be in a range from about 40° to about 80°, or from about 50° to about 70° (e.g., about 60°) relative to horizontal (e.g., a horizontal line running across the bottom of lower connecting member 214). The lower inside angle 350 may be in a range from about 10° to about 50°, or in a range from about 20° to about 40° (e.g., about 30°) relative to horizontal (e.g., a horizontal line running across the bottom of lower connecting member 214). The upper outside angle 352 may be in a range from about 30° to about 70°, or in a range from about 40° to about 60° (e.g., about 50°) relative to horizontal (e.g., a horizontal line running across the bottom of lower connecting member 214). The upper inside angle 354 may be in a range from about 20° to about 60°, or in a range from about 30° to about 50° (e.g., about 40°) relative to horizontal (e.g., a horizontal line running across the bottom of lower connecting member 214). In an embodiment the lower and upper outside angles 348 and 352 may be approximately equal (and in opposite directions), being angled towards one another, as shown. In another embodiment, the angles may differ (e.g., upper greater than lower, or lower greater than upper). These angulated upper and lower thickened corner bumpers 238 extend outwardly, towards the bony structure bounding the vestibule. Similar anatomical angulation may be provided on the right side upper and lower bumpers 238.

Figure 14A:
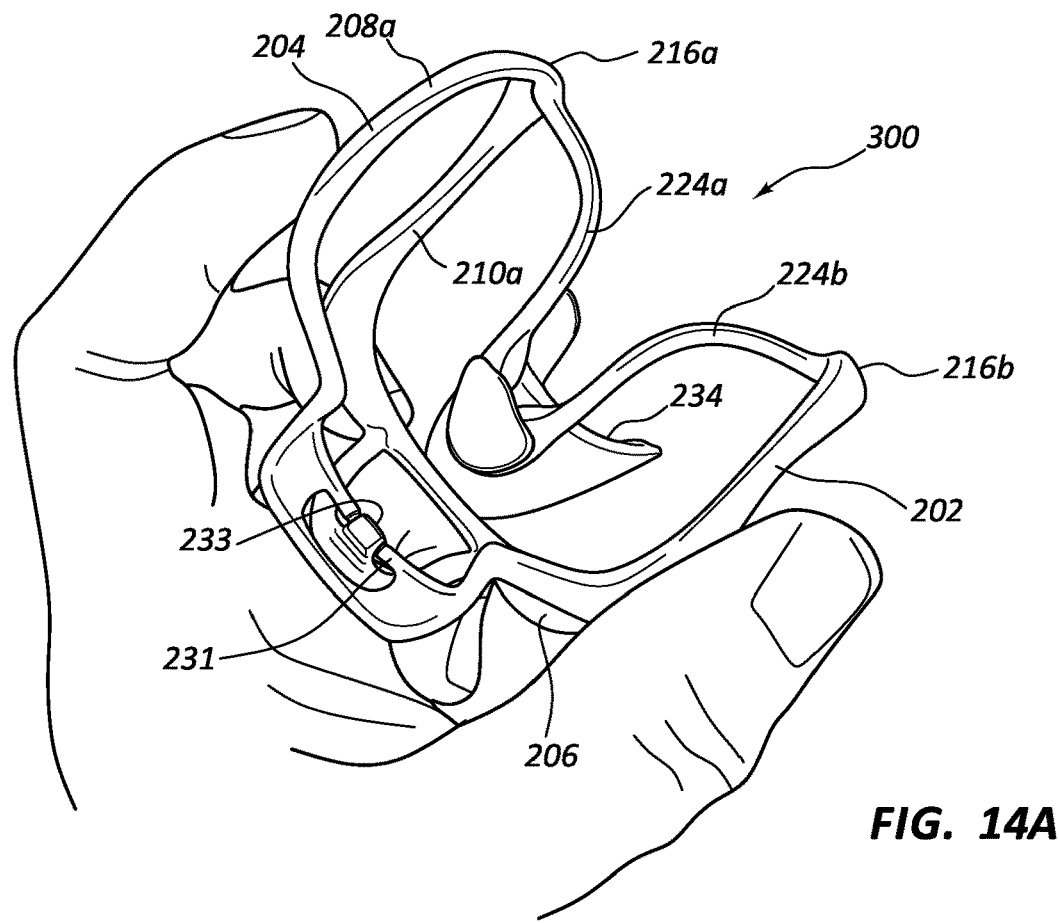
FIG. 14A shows the device of FIG. 12A, with the frame partially collapsed from side-to-side.
Figure 14B:
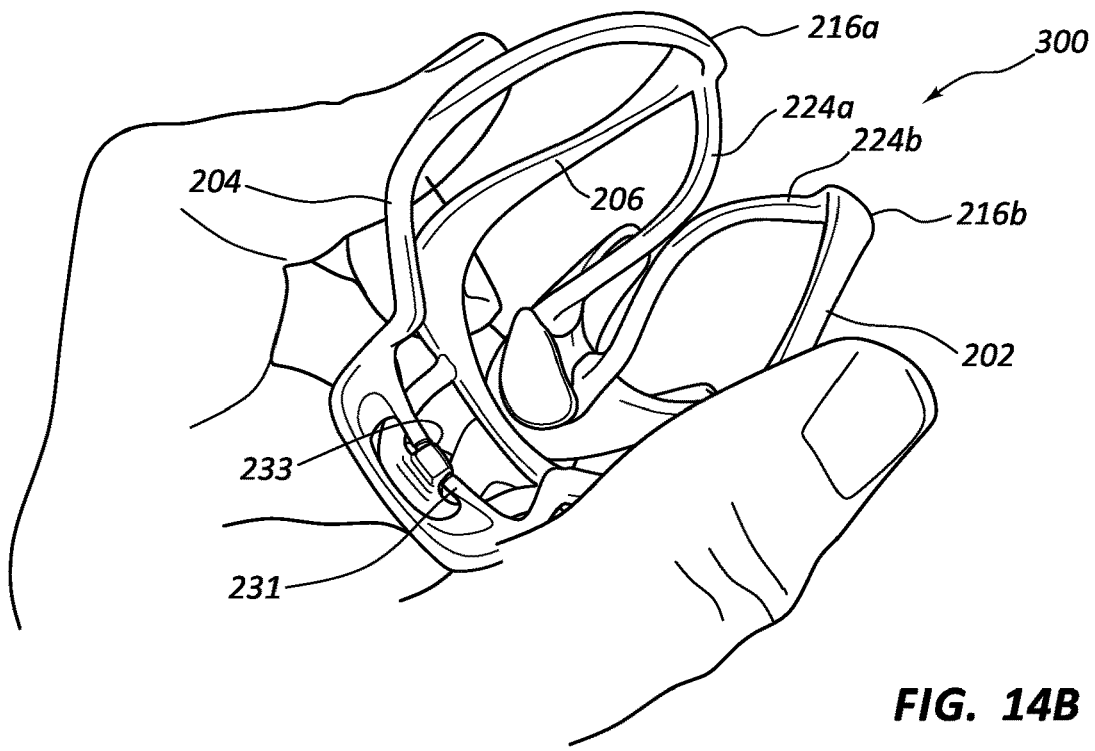
FIG. 14B shows the device of FIG. 14A, with the frame further collapsed from side-to-side.

In addition to this collapsibility in a top to bottom dimension, the device may also be configured as described above, to collapse side-to-side. FIGS. 14A and 14B illustrate how a practitioner may collapse the device side-to-side, due to the flexible, spring-like characteristics of the frame 202. Where no crossbar is present (e.g., see FIG. 12B), the posterior ends 216 may be pressed towards one another, to collapse the device in a side-to-side dimension. Even where a crossbar 224 is present, as seen in FIG. 12A and FIGS. 14A-14B, the crossbar 224 may include an anteriorly curved central portion 226, which facilitates side-to-side collapse as the posterior ends of the device are pushed towards one another. The two posteriorly curved portions 224a and 224b may also facilitate side-to-side collapse. During collapse, the curved portion 226 advances forwardly, e.g., and may pass over or under lower anterior connecting member 214, depending on the degree of side-to-side collapse. Posteriorly curved members 224a and 224b may also move closer together, accommodating the collapse, as seen in FIGS. 14A and 14B. As seen in FIG. 14A, as posterior arced regions 216 are pressed towards one another, the ends of curved members 224a, 224b adjacent central curve 226 may become increasingly parallel to one another, and then possibly eventually touching, as seen in FIG. 14B, depending on the degree of side-to-side collapse. Such a top to bottom and side-to-side collapsed configuration as seen in FIG. 14A or 14B is particularly compact, making it quite easy to insert into a patient's mouth without requiring the patient to open their mouth to an uncomfortable degree.

Figure 15A:
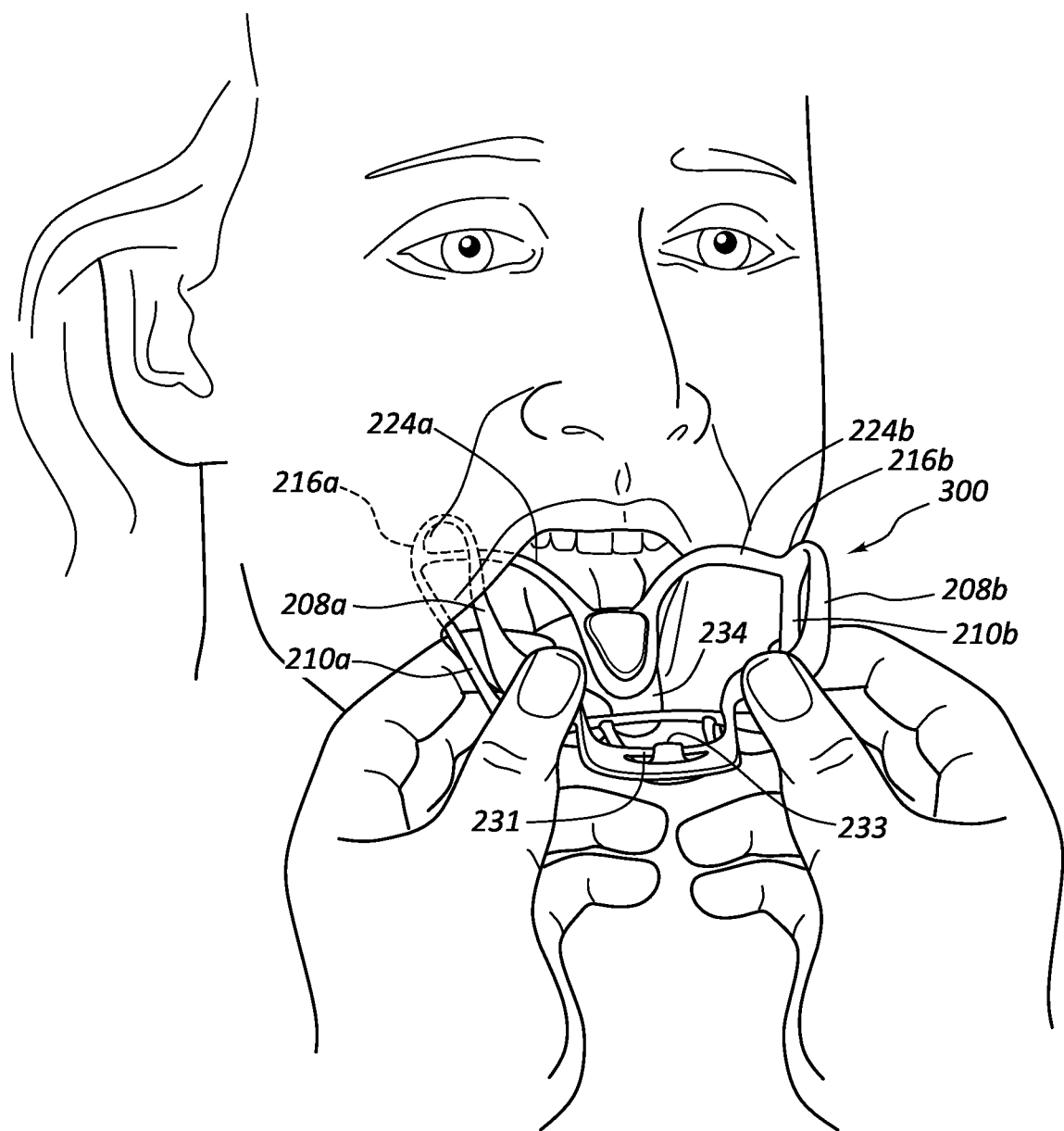
FIGS. 15A-15B show how the device of FIG. 12A may be placed into a person's mouth using the top to bottom collapsibility of the device, with little or no reliance on the side-to-side collapsibility of the device.
Figure 15B:
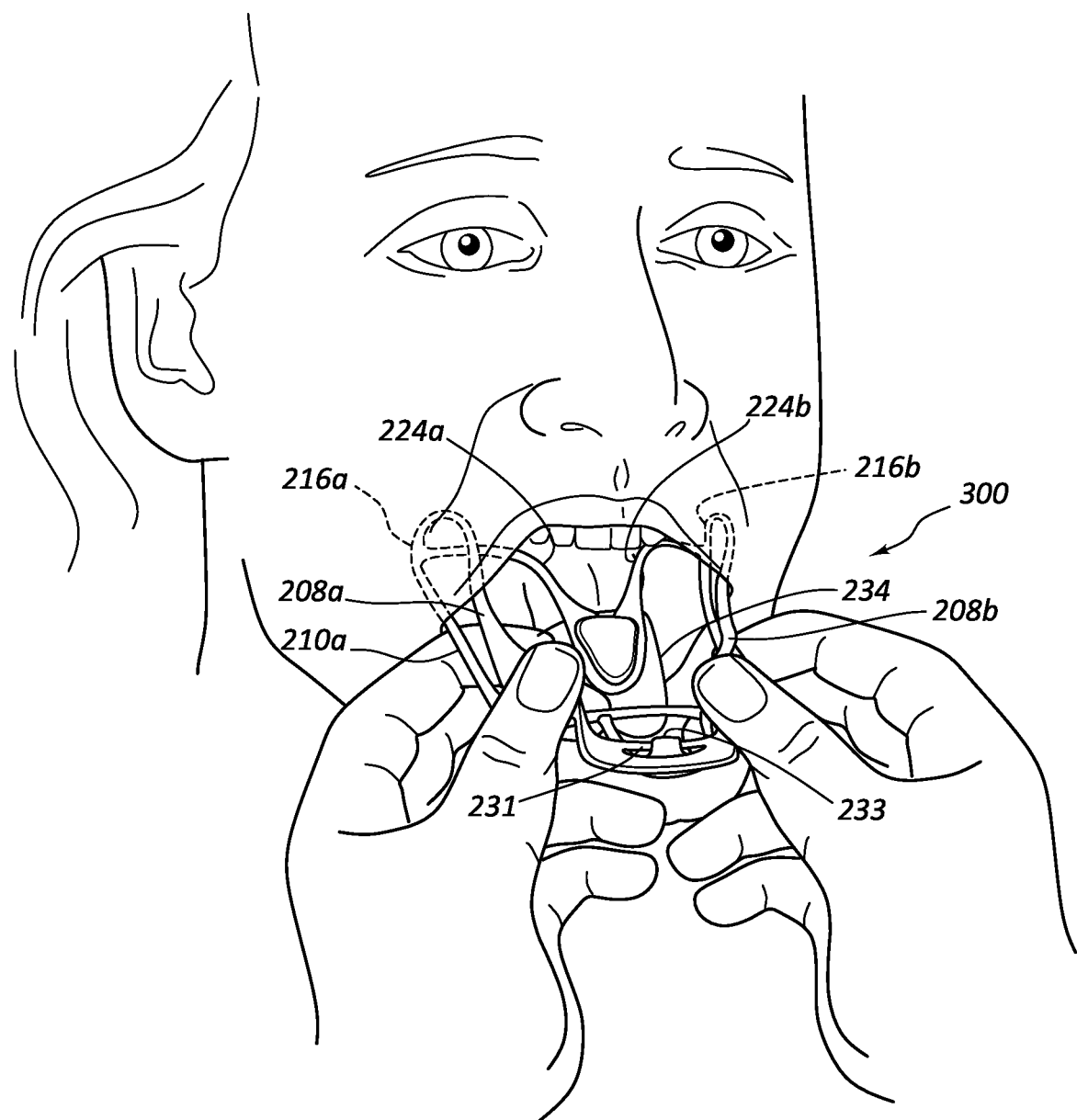
Figure 16A:
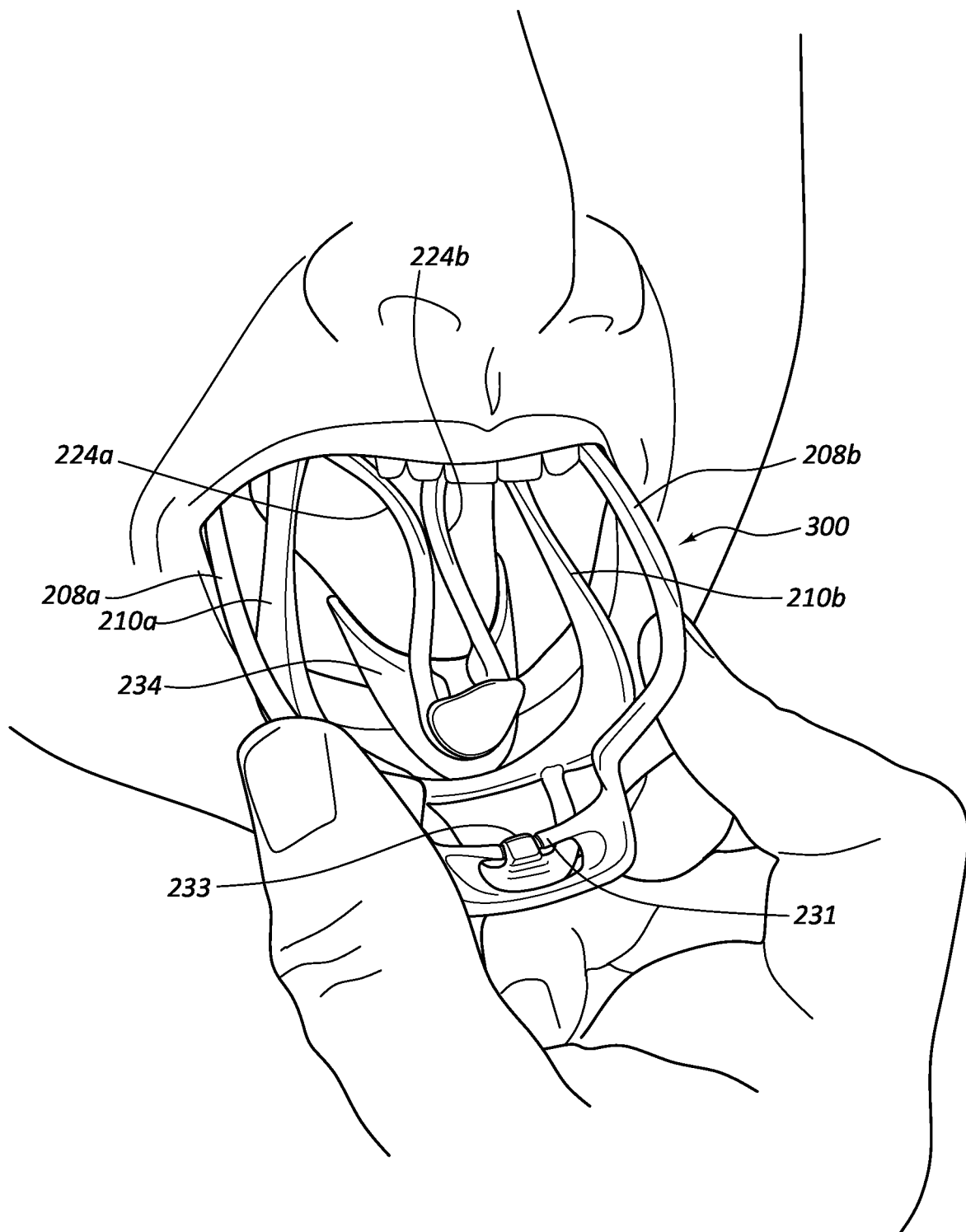
FIG. 16A shows how the device of FIG. 12A may be placed into a person's mouth using both the top to bottom and side-to-side collapsibility of the device.

FIGS. 15A-15B illustrate one exemplary method of insertion, while FIG. 16A illustrates another method. As shown in FIG. 15A, the practitioner may collapse the expansion device 300 top to bottom, while employing little if any of the side-to-side collapsibility of the expansion device. Rather, the practitioner may wish to insert one posterior arced region 216 of the expansion device 300 into one side of the mouth followed by shoehorning the other posterior arced region 216 into the mouth. Because the device is collapsed top to bottom during such insertion, the patient is not required to open their mouth to an uncomfortable degree, but may simply insert one posterior region (e.g., 216a) towards the rear of the vestibule or oral cavity, and then swing the other posterior region (e.g., 216b) into place, towards the opposite vestibule. If desired, while swinging the second posterior end into place, some of the device's side-to-side collapsibility may be employed, should the practitioner simply compress the two posterior ends 216 towards one another.

FIG. 16A illustrates another method of insertion, where no such shoehorning of one posterior side and then the other may be employed, but where the expansion device is collapsed top to bottom (e.g., and latched in that collapsed state), and then also collapsed side-to-side as seen in FIGS. 14A and 14B. By employing the latch, such may easily be achieved with a single hand. The width of the expansion device is so small when so collapsed, that it easily fits into the mouth of a patient, without requiring them to open their mouth to an uncomfortable degree. By way of example, the top to bottom collapse may reduce the height of the device from about 85-100 mm (expanded) to about 30 mm (e.g., a reduction of 50% or more, or 60% or more (e.g., about 50% to about 70%)). The side-to-side collapse may reduce the width of the device from about 100 mm (expanded) to about 60-70 mm (e.g., a reduction of about 30% to about 40%). As will be apparent the majority (perhaps nearly all) of the side-to-side collapse occurs posteriorly, making the posterior collapsed width similar to that of the anterior widths 122 and 122' described in conjunction with FIGS. 1 and 6. Such decreased height and width allows the multi-dimensionally collapsed expansion device to easily be inserted into the mouth of the patient, as seen in FIG. 16A. No uncomfortable opening of the mouth, or uncomfortable side-to-side stretching of the lips is needed.

In either case, once inserted and expanded, the expansion device "floats" within the patient's mouth, with the side members 208, 210 of the upper and lower frame portions 204 and 206 resting in the upper and lower vestibules of the patient, between the alveolar ridge and the lips or cheeks. The posterior crossbar 224 (if present) crosses from one side of the dental arches to the other, in a retromolar region, behind the molars of the patient. As described above, the crossbar 224 may bear against the soft tissue covering the mandibular ramus R of the patient, exerting a forward force on the device, pushing it forward. FIGS. 16B-18D show how the soft tissue covering the mandibular ramus R is abutted by the posteriorly curved portions of crossbar 224, providing the desired posterior loading. Such posterior loading further flares the upper lips forward (in the z-dimension) and upward (in the y-dimension) and the cheeks outward (in the x-dimension). The lower lips are similarly further flared forward, (in the z-dimension), downward (in the y-dimension), with the cheeks being flared outward (in the x-dimension). Such posterior loading thus widens the working field. Only the lip protecting members of the expansion device may reside outside of the mouth (over the center of the upper and lower lips), with the other portions of the frame being received within the mouth. Side members 208 and 210 may be received within the upper and lower facial vestibules, and the upper and lower anterior connecting members may be received within the upper and lower anterior vestibules. No portion interferes with access to the dental arches. If a posterior crossbar is present, the crossbar 224 passes retromolarly, between the posterior teeth and the ramus.

Figure 16B:
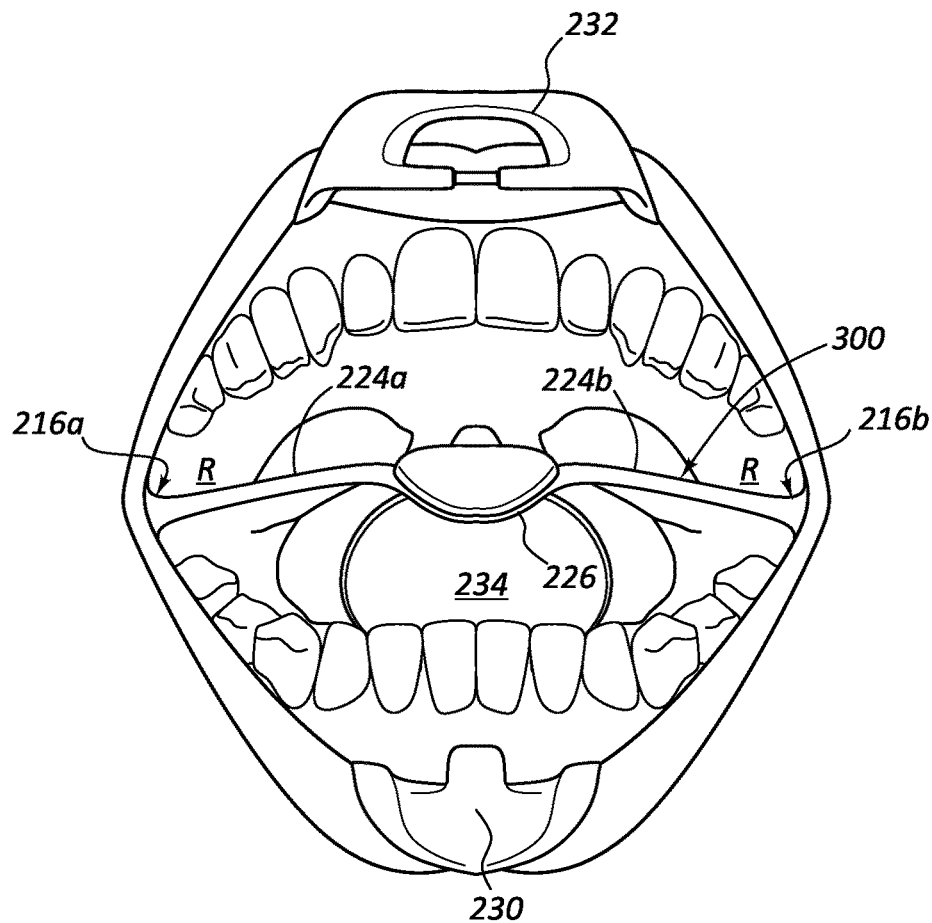
FIG. 16B shows the device of FIG. 12A in the mouth, with the mouth open, e.g., as placed using either the method of FIGS. 15A-15B or that of FIG. 16A.
Figure 16C:
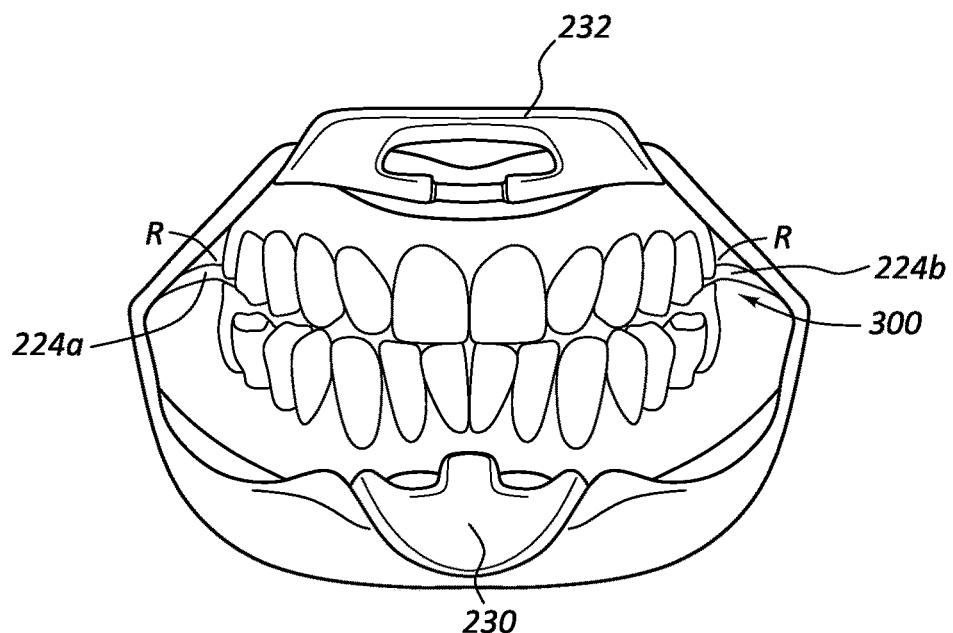
FIG. 16C is similar to that of FIG. 16B, but showing the person's jaw being closed, with the device in the mouth.

FIGS. 16B and 16C illustrate how when positioned within the person's mouth, the patient still has full movement of their jaw, so as to allow the user to open and close their jaw as normally possible. FIG. 16B shows the jaw open, with FIG. 16C showing the jaw closed. No portion of the frame interferes with this ability to fully open and fully close the jaw, while the expansion device is in the mouth. As seen in FIG. 16C, the expansion device holds the lips comfortably retracted or expanded from the dental arches, so that the teeth of both arches are easily and fully visible, even with the jaw closed. As seen, the frame inflates, displaces, and flares the patient's cheeks and lips away from the teeth, so that no contact is made between the frame and the teeth or gums. The frame may be devoid of any structures that would obstruct access to the teeth when the frame is expanded, and that would prevent the patient from fully biting down and making full occlusal contact between the person's upper and lower teeth. For example, the frame may be devoid of any structures interconnecting the upper and lower frame portions apart from the posterior crossbar, so as to not impede access to the person's teeth and gums when the frame is expanded in the mouth. The posterior crossbar 224 does not impede access, as it passes across the retromolar region, so as to not interfere with the $2^{nd}$ or even the $3^{rd}$ molars, if present. In addition, no anterior ring is present that circles the perimeter of the patient's mouth opening, which uncomfortably stretches the lips side-to-side, and which can interfere with access to certain teeth (e.g., canines and bicuspids, as it passes from the upper to lower portions of the oral cavity).

The frame may be flexible when expanded in the mouth so as to permit all typical functional movements of the person's mandible in x-axis (side-to-side), y-axis (up and down), and z-axis directions (forward and backward). In other words, the person is able to close the mandible (generally a y-axis movement), as well as move the mandible in any other typical motion possible when the frame is not expanded within the mouth. The frame simply floats within the vestibule portion of the mouth, between the cheeks/lips and the dental arch (teeth and gums in the alveolar ridge), inflating the cheeks and lips outwardly and forwardly, but permits normal movement and functioning of the jaw when expanded within the mouth. Of course, the cheeks and lips are held outward and forward, inflated away from their normal positions when a mouth is closed with no such device inserted.

In an embodiment, the frame does not fully stretch the lips side-to-side around the person's mouth, to their limits, but rather holds them open, and flares them forward, to a comfortable degree, all while providing a widened working field for the practitioner. In other words, the frame inflates and flares the lips forwardly and away from the anterior teeth in a z-axis direction without fully stretching the lips side-to-side in an x-axis direction. This permits the persons lips and cheeks to be asymmetrically deformed, facilitating enlargement of the working field on a particular side of the mouth. For example, many existing retraction devices grab the lips on opposite sides of the mouth, pulling them apart side-to-side. As seen in FIGS. 17A and 17B, the present devices do not so stretch the lips, but allow further expansion of one side or the other. In other words, Because of the comfortable expansion of the lips and cheeks that is instead provided, the practitioner can reach into the mouth and pull the lips to one side or the other, expanding one side or the other side asymmetrically, as seen in FIGS. 17A-17B. This permits asymmetric deformation of the lips to either side, facilitating further enlargement of the working field on a particular side of the mouth. In addition, while so doing, as the expansion device itself "floats" within the mouth, such movements or expansions by the practitioner generally does not move the device, which remains generally in the same position in the mouth.

As will be apparent from the described methods and from FIGS. 13A-17B, the flexible spring-like frame provides an insertion configuration wherein the frame is inwardly collapsible in multiple dimensions, e.g., at least from top to bottom, and from side-to-side. During such collapse in two dimensions, some collapse in the third dimension (z-axis—forward to back) may also occur. The flexible spring-like frame also provides a second, expanded configuration, where the frame is outwardly expandable by opening up from top to bottom and from side-to-side. The expanded configuration provides retraction of a person's cheeks and lips to create an enlarged working field that permits unobstructed access to both upper and lower dental arches, including all teeth from the second molar position forward. The upper frame portion 204 of the frame is configured to extend continuously about the upper dental arch, from a first posterior arced region (e.g., 216a) that is behind a second molar position on one side of the upper dental arch to a second posterior arced region (e.g., 216b) that is behind a second molar position on an opposite side of the upper dental arch. The lower frame portion 206 is configured to continuously extend about the lower dental arch, from the first posterior arced region (e.g., 216a) that is also behind the second molar position on one side of the lower dental arch to the second posterior arced region (e.g., 216b) that is also behind the second molar on the opposite side of the lower dental arch. The first and second posterior regions 216 join the upper and lower frame portions 204, 206 to one another, and provide a bendable radius on either side (e.g., about arced region 216a, along side members 208a, 210a, and about end 216b, along side members 208b, 210b) that facilitates the insertion configuration, where the frame is inwardly collapsible from top to bottom, as well as the expanded configuration, where the frame is outwardly expanded by opening from top to bottom. The posterior arced regions 216 may also be collapsed side-to-side, towards one another, facilitating side-to-side collapse of the frame, and its subsequent expansion upon release of the collapsing force. The posterior regions 216 may be thickened in the vicinity of the frame where such ends are located, so as to better resist bending at that particular point, distributing the bending forces along a greater length on either side of the arced region, into the side members. Such thickened regions 240 also help to open the frame upward, (i.e., top to bottom), creating increased resistance to closing of the jaw-like frame. The frame components, particularly the side members 208, 210, thus include relatively thinner cross-sections through essentially the middle portion of each side member of the upper and lower frame portions, causing much of the bending to occur within these thinner frame structures.

The shape of the side members 208, 210, upper and lower anterior connecting members 212, 214, and the frame 202 in general, may be configured to follow the contours of the portions of the vestibule into which any given particular portion is to be received. For example, the side members 208, 210 of the upper and lower frame portions may be curved and shaped anatomically, for receipt into the facial vestibule on either side of the dental arches. Similarly, the anterior corner bumpers 238 at the anterior ends of each side member may be shaped, curved, and sized for receipt into the corners of the anterior portions of the upper and lower vestibules, at the front of the dental arches. Because of differences in the upper and lower dental arches, and in the upper and lower vestibules associated with such arches, the upper and lower frame portions may be differently sized and shaped. For example, the lower frame 206 may be overall shorter, and narrower at its anterior front width, while the upper frame portion 208 is overall longer, and wider at its anterior front width. The side members 208 of the upper frame portion may be shorter than the side members 210 of the lower frame portion, and the thickened anterior corner bumpers 238 of the upper frame may be more rounded, and larger than those of the lower frame portion. All such differences better accommodate the actual anatomy of the person, providing better comfort when the frame is expanded within the vestibules.

The upper and lower frame portions (particular the side members of each) expand the upper and lower facial vestibules (e.g., adjacent the cheeks) laterally (side-to-side—in the x direction), flaring the cheeks outwardly as the frame resides within the vestibule, expanding and flaring the cheeks outward, like a tent. The upper and lower anterior vestibules are similarly expanded, but in a forward direction (in the z-direction), flaring the lips forward. The upper and lower anterior vestibules are also expanded in the y-direction, retracting the upper lips upwardly and the lower lips downwardly In other words, the cheeks are expanded in the x-direction, while the lips are generally expanded in the z and y directions.

Figure 18D:
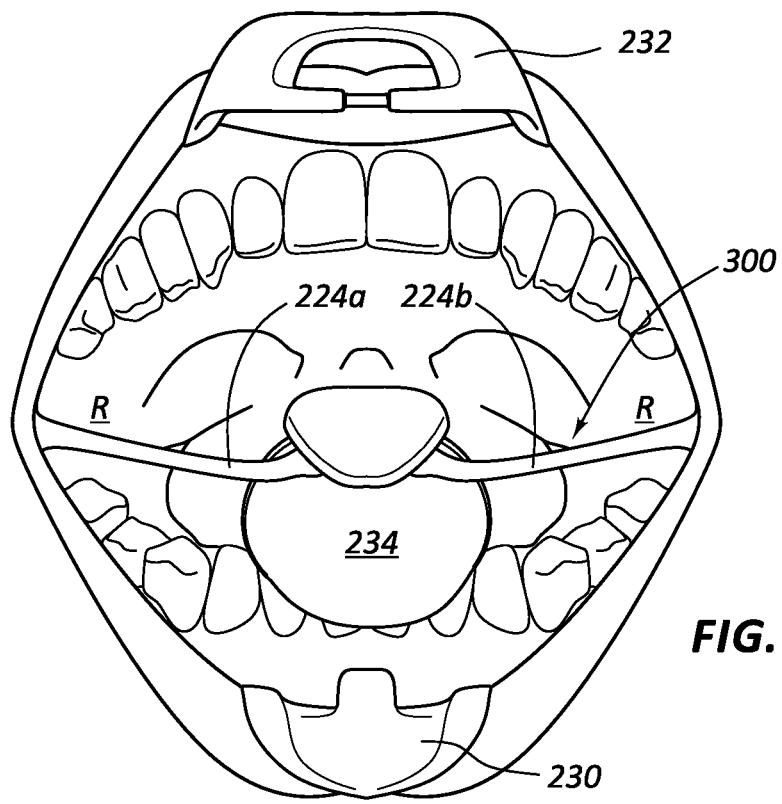

FIGS. 18A-18D illustrate how the tongue guard 234 may gently house the tongue, so as to reduce its interference with the practitioner's working field, protecting the tongue from injury, but at the same time allowing the patient to move the tongue up, down, or to either side. The tongue guard may hold and guide the person's tongue, but may not significantly push the tongue back, flatten the tongue, or thicken the tongue. Flattening or thickening the tongue (by pushing it down or back) may increase risk of injury, as it increases the surface area of the tongue as a target for a drill or other dental tool. Many other existing tongue guard devices tend to forcefully push the tongue back, flatten the tongue, or thicken the tongue, which can be uncomfortable to the patient, while also increasing injury risk. The tongue guard may hold the tongue in place, even if the jaw is closed, a characteristic which also differs from many existing retraction devices. For example, FIGS. 18A-18D shows how the patient may move the distal tip of the tongue within tongue guard 234 to the right (FIG. 18A), to the left (FIG. 18B), up (FIG. 18C) or down (FIG. 18D). Tongue guard 234 holds and guides the distal tip of the tongue, while still permitting such movement by the patient. The tongue is not significantly flattened or thickened, particularly the exposed portions thereof.

As used in this specification and the appended claims, the singular forms "a," "an" and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A frame of a cheek and lip expansion device configured to extend about dental arches of a user, the frame comprising:

an upper frame portion including a first upper side member, a second upper side member, a first upper connecting portion, and a second upper connecting portion;

a lower frame portion including a first lower side member, a second lower side member, a first lower connecting portion, and a second lower connecting portion;

a first upper thickened structure disposed between the first upper side member and the first upper connecting portion, the first upper thickened structure having an enlarged cross-section relative to adjacent portions of the first upper side member and the first upper connecting portion;

a second upper thickened structure disposed between the second upper side member and the second upper connecting portion, the second upper thickened portion having an enlarged cross-section relative to adjacent portions of the second upper side member and the second upper connecting portion;

a first lower thickened structure disposed between the first lower side member and the first lower connecting portion, the first lower thickened structure having an enlarged cross-section relative to adjacent portions of the first lower side member and the first lower connecting portion; and a second lower thickened structure disposed between the second lower side member and the second lower connecting portion, the second lower thickened structure having an enlarged cross-section relative to adjacent portions of the second lower side member and the second lower connecting portion.

2. The frame of claim 1, further comprising:

a first posterior thickened structure disposed between the first upper side member and the first lower side member, the first posterior thickened structure having an enlarged cross-section relative to the adjacent portions of the first upper side member and the first lower side member; and a second posterior thickened structure disposed between the second upper side member and the second lower side member, the second posterior thickened structure having an enlarged cross-section relative to the adjacent portions of the second upper side member and the second lower side member;

wherein:

the first upper side member, the first lower side member, and the first posterior thickened structure form a first bendable radius; and the second upper side member, the second lower side member, and the second posterior thickened structure form a second bendable radius.

3. The frame of claim 1, further comprising a posterior crossbar that connects the first posterior thickened structure and the second posterior thickened structure.

4. The frame of claim 3, wherein:

the posterior crossbar comprises a first and a second posteriorly curved members; and a middle portion of the posterior crossbar is anteriorly curved to facilitate inward collapse of the frame from side-to-side as the first thickened structure and the second thickened structure posterior are pressed towards one another.

5. The frame of claim 1, wherein the first upper connecting member includes a greater anterior width than an anterior width of the first lower connecting member.

6. The frame of claim 1, further comprising:
a first posterior frame arched region including the first upper side member, the first posterior thickened structure, and the first lower side member; and
a second posterior frame arched region including the second upper side member, the second posterior thickened structure, and the second lower side member.

7. The frame of claim 6, wherein:
the first posterior thickened structure of the first posterior frame arched region being resistant to bending; and
the second posterior thickened structure of the second posterior frame arched region being resistant to being.

8. The frame of claim 6, wherein the first upper thickened structure, the second upper thickened structure, the first lower thickened structure, and the second lower thickened structure are comprised of an elastomeric material disposed over a portion of the upper frame portion and a portion of lower frame portion, respectively.

9. A cheek and lip expansion device, the device comprising:
a first upper side member;
a first upper connecting portion;
a first upper thickened structure disposed between the first upper side member and the first upper connecting portion, the first upper thickened structure having an enlarged cross-section relative to adjacent portions of the first upper side member and the first upper connecting portion;
a second upper side member;
a second upper connecting member;
a second upper thickened structure disposed between the second upper side member and the second upper connecting portion, the second upper thickened structure having an enlarged cross-section relative to adjacent portions of the second upper side member and the second lower connecting member;
a first lower side member;
a first lower connecting portion;
a first lower thickened structure disposed between the first lower side member and the first lower connecting portion, the first lower thickened structure having an enlarged cross-section relative to adjacent portions of the first lower side member and the first lower connecting portion;
a second lower side member;
a second lower connecting portion; and
a second lower thickened structure disposed between the second lower side member and the second lower connecting portion, the second lower thickened structure having an enlarged cross-section relative to adjacent portions of the second lower side member and the second lower connecting portion.

10. The device of claim 9, further comprising:
a first posterior thickened structure disposed between the first upper side member and the first lower side member, the first posterior thickened structure having an enlarged cross-section relative to the adjacent portions of the first upper side member and the first lower side member; and
a second posterior thickened structure disposed between the second upper side member and the second lower side member, the second posterior thickened structure having an enlarged cross-section relative to the adjacent portions of the second upper side member and the second lower side member.

11. The device of claim 10, further comprising a posterior crossbar connected to a first posterior frame arched region and a second posterior frame arched region.

12. The device of claim 11, wherein:
the posterior crossbar comprises a first and a second posteriorly curved members; and
a middle portion of the posterior crossbar is curved to facilitate inward collapse of the frame from side-to-side as the first thickened structure and the second thickened structure posterior are pressed towards one another.

13. The device of claim 11, wherein:
the first posterior arched region includes at least a portion of the first upper side member, the first posterior thickened structure, and the first lower side member;
the second posterior arched region includes at least a portion of the second upper side member, the second posterior thickened structure;
the posterior crossbar is connected to the first posterior arched region by one or more gussets; and
the posterior crossbar is connected to the second posterior arched region by one or more gussets.

14. The device of claim 10,
wherein the first upper thickened structure, the second upper thickened structure, the first lower thickened structure, and the second lower thickened structure are comprised of an elastomeric material disposed over a portion of an upper portion of a frame and a portion of a lower portion of the frame.

15. The device of claim 9, further comprising:
a first posterior frame arched region including the first upper side member, the first posterior thickened structure, and the first lower side member; and
a second posterior frame arched region including the second upper side member, the second posterior thickened structure, and the second lower side member.

16. The device of claim 15, wherein:
the first posterior thickened structure of the first posterior frame arched region being resistant to bending; and
the second posterior thickened structure of the second posterior frame arched region being resistant to being.

17. The device of claim 15, wherein:
the first upper thickened structure being resistant to bending;
the second upper thickened structure being resistant to bending;
the first lower thickened structure being resistant to bending;
the second lower thickened structure being resistant to bending;
the first posterior thickened structure being resistant to bending; and
the second posterior thickened structure being resistant to being.

18. A frame of a cheek and lip expansion device, the frame comprising:
an upper frame portion including a first upper side member, a second upper side member, a first upper connecting portion, and a second upper connecting portion;
a lower frame portion including a first lower side member, a second lower side member, a first lower connecting portion, and a second lower connecting portion;
a first upper thickened structure disposed between the first upper side member and the first upper connecting portion, the first upper thickened structure having an enlarged cross-section relative to adjacent portions of the first upper side member and the first upper connecting portion;

a second upper thickened structure disposed between the second upper side member and the second upper connecting portion, the second upper thickened portion having an enlarged cross-section relative to adjacent portions of the second upper side member and the second upper connecting portion;

a first lower thickened structure disposed between the first lower side member and the first lower connecting portion, the first lower thickened structure having an enlarged cross-section relative to adjacent portions of the first lower side member and the first lower connecting portion; and a second lower thickened structure disposed between the second lower side member and the second lower connecting portion, the second lower thickened structure having an enlarged cross-section relative to adjacent portions of the second lower side member and the second lower connecting portion;

a first posterior thickened structure disposed between the first upper side member and the first lower side member, the first posterior thickened structure having an enlarged cross-section relative to adjacent frame portions;

a second posterior thickened structure disposed between the second upper side member and the second lower side member, the second posterior thickened structure having an enlarged cross-section relative to adjacent frame portions;

wherein:
the first and the second posterior thickened structures are resistant to bending; and
the first and the second posterior thickened structures are configured to transfer a flexing force acting to press a first frame portion towards a second frame portion.

19. The frame of claim 18, wherein:
the first frame portion and the second frame portion are configurable in a collapsed arrangement in which an anterior portion of the first frame portion is bent towards an anterior portion of the second frame portion responsive to imposition of the flexing force;
the first frame portion and the second frame portion are further configurable in an expanded arrangement responsive to removal of the flexing force; and
in the collapsed arrangement, the flexing force is substantially transferred from to the adjacent frame portions such that the adjacent frame portions flex.

20. The frame of claim 18, further comprising a posterior crossbar that connects the first posterior thickened structure to the second posterior thickened structure, wherein:
the posterior crossbar is configured for inward collapse from side-to-side as the first posterior thickened structure and the second posterior thickened structure are pressed towards one another; and
the frame is devoid of any structures interconnecting the first and the second frame portions apart from the posterior crossbar.

* * * * *